(12) United States Patent
Ehringer et al.

(10) Patent No.: US 9,066,866 B2
(45) Date of Patent: *Jun. 30, 2015

(54) DIRECT CELLULAR ENERGY DELIVERY SYSTEM

(75) Inventors: William D. Ehringer, Charleston, IN (US); Sufan Chien, Floyd Knobbs, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,546

(22) Filed: Jun. 17, 2011

(65) Prior Publication Data

US 2011/0311442 A1 Dec. 22, 2011

Related U.S. Application Data

(63) Continuation of application No. 11/349,023, filed on Feb. 7, 2006, now abandoned, which is a continuation-in-part of application No. 10/397,048, filed on Mar. 25, 2003, now Pat. No. 7,056,529.

(60) Provisional application No. 60/380,762, filed on May 14, 2002.

(51) Int. Cl.
| | |
|---|---|
| *A61K 9/127* | (2006.01) |
| *A61K 9/00* | (2006.01) |
| *A61K 31/7076* | (2006.01) |
| *A61K 38/28* | (2006.01) |
| *A61K 51/12* | (2006.01) |
| *A61K 49/00* | (2006.01) |
| *A61K 31/59* | (2006.01) |
| *A61K 31/355* | (2006.01) |
| *A61K 31/07* | (2006.01) |
| *A61K 31/575* | (2006.01) |

(Continued)

(52) U.S. Cl.
CPC ............. *A61K 9/127* (2013.01); *Y10S 977/726* (2013.01); *Y10S 977/907* (2013.01); *A61K 9/0019* (2013.01); *A61K 31/7076* (2013.01); *A61K 38/28* (2013.01)

(58) Field of Classification Search
None
See application file for complete search history.

(56) References Cited

U.S. PATENT DOCUMENTS 4,704,355 A * 11/1987 Bernstein ..................... 435/6.12
4,857,319 A * 8/1989 Crowe et al. ................. 424/94.1

(Continued)

FOREIGN PATENT DOCUMENTS

WO WO 0066137 A1 * 11/2000

OTHER PUBLICATIONS

A Chavez, M Pujol, MA Alsina, Y Cajal. "Membrane Fusion Introduced by a Lipopeptidic Epitope from VP3 Capside Protein of Hepatitis A Virus." Luminescence, vol. 16, 2001, pp. 135-143.*

(Continued)

*Primary Examiner* — Isaac Shomer
(74) *Attorney, Agent, or Firm* — Stites & Harbison PLLC; Mandy Wilson Decker

(57) ABSTRACT

A lipid vesicle comprising a phospholipid which is a stable vesicle former and at least one unstable vesicle forming member, wherein the unstable vesicle forming member is selected from the group consisting of a polar lipid which is not a stable vesicle former, a PEG, a raft former and a fusion protein is provided. The vesicle can further comprise a biomolecule, such as for example ATP. Methods of using the vesicle for delivery of biomolecules are also provided.

51 Claims, 6 Drawing Sheets

(51) Int. Cl.
  *A61K 31/56* (2006.01)
  *A61K 38/02* (2006.01)
  *A61K 38/48* (2006.01)
  *A61K 31/70* (2006.01)
  *A61K 38/18* (2006.01)

(56) References Cited

U.S. PATENT DOCUMENTS

| | | | | | |
|---|---|---|---|---|---|
| 5,162,201 | A | * | 11/1992 | Imamura et al. | 435/19 |
| 5,542,935 | A | * | 8/1996 | Unger et al. | 604/190 |
| 5,582,839 | A | * | 12/1996 | McCarty | 424/489 |
| 5,674,528 | A | * | 10/1997 | Ogata et al. | 424/450 |
| 5,783,566 | A | * | 7/1998 | Mislick | 514/44 R |
| 5,811,406 | A | * | 9/1998 | Szoka et al. | 514/44 R |
| 5,874,075 | A | * | 2/1999 | Collins et al. | 424/85.1 |
| 5,965,542 | A | * | 10/1999 | Wasan et al. | 514/44 R |
| 6,110,666 | A | * | 8/2000 | Grosveld et al. | 435/6.12 |
| 6,130,186 | A | * | 10/2000 | Ward et al. | 504/365 |
| 6,132,763 | A | * | 10/2000 | Fisher | 424/450 |

OTHER PUBLICATIONS

N Neveux, JPD Bandt, E Fattal, L Hannoun, R Poupon, JC Chaumeil, J Delattre, LA Cynober. "Cold Preservation Injury in Rat Liver: Effect of LIposomally-Entrapped Adenosine Triphosphate." Journal of Hepatology, vol. 33, 2000, pp. 68-75.*

CR Scholfield. "Composition of Soybean Lecithin." Journal of the American Oil Chemists' Society, vol. 58, No. 10, Oct. 1981, pp. 889-892.*

I Wrobel, D Collins. "Fusion of Cationic Liposomes with Mammalian Cells Occurs After Endocytosis." Biochimica et Biophysica Acta, vol. 1235, 1999, pp. 296-304.*

SM Berge, LD Bighley, DC Monkhouse. "Pharmaceutical Salts." Journal of Pharmaceutical Sciences, vol. 66 No. 1, Jan. 1977, pp. 1-19.*

M Jansson, RL Thurmond, TP Trouard, MF Brown. "Magnetic alignment and orientational order of dipalmitoylphosphatidylcholine bilayers containing palmitoyllysophosphatidylcholine." Chemistry and Physics of Lipids, vol. 54, 1990, pp. 157-170.*

Molina et al., "The Stability of Lyophilized Lipid/DNAComplexes during Prolonged Storage," J Pharm Sci, Sep. 2004, vol. 93(9), pp. 2259-2273.

Kang et al., "Effects of cellular ATP depletion on glucose transport and insulin signaling in 3T3-L1 adipocytes," Am J Physiol Endocrinol Metab, Mar. 2001, vol. 280(3), pp. E428-E435.

Nicola et al., "Roles for Endocytosis and Low pH in Herpes Simplex Virus Entry into HeLa and Chinese Hamster Ovary Cells," J. Virol, May 2003, vol. 77 No. 9, pp. 5324-5332.

Selvi et al., "ATP driven clathrin dependent entry of carbon nanospheres prefer cells with glucose receptors," Journal of Nanobiotechnology, 2012, 10:35.

* cited by examiner

ATP-SUV	Control

DIRECT CELLULAR ENERGY DELIVERY SYSTEM

RELATED APPLICATIONS

This application is a continuation patent application which claims the benefit of the filing date of U.S. patent application Ser. No. 11/349,023 filed on Feb. 7, 2006, which is a continuation-in-part of U.S. patent application Ser. No. 10/397,048 filed on Mar. 25, 2003, now U.S. Pat. No. 7,056,529, which claims priority to U.S. Provisional Patent Ser. No. 60/380,762 filed May 14, 2002, the disclosure of each of which is incorporated herein by reference in its entirety.

GOVERNMENT INTEREST

This invention was made with government support under Grant Nos. HL 64186-01A1-01, HL073578-01, DK067702-01 awarded by the National Institutes of Health. The government has certain rights in the invention.

TECHNICAL FIELD

The presently disclosed subject matter relates to lipid vesicles useful for the delivery of biomolecules to cells and methods for using same.

BACKGROUND

Cells and tissues can become deficient in particular biomolecules due to, for example, stressful environmental conditions. In order for the cells and tissues to survive, the levels of deficient biomolecules must be raised within the cells and tissues to meet metabolic demand. For example, ATP is a biomolecule relied upon by cells as a primary source of energy and an increased metabolic demand or shortfall in supply of ATP to cells can result in death of the cells if demand is not met quickly.

ATP is the fuel that powers all cells-animal, plants, bacteria, fungi, etc. Such as a car without gas, humans and other creatures with an empty ATP "tank" do not go. In fact, they die. The energy derived from the breakdown of nutrients is ultimately conserved in the high energy phosphate bonds of ATP. When these bonds are broken, they provide accessible energy to cells, tissues, organs and organ systems. Cells constantly synthesize and metabolize ATP. ATP can be produced either aerobically through oxidative phosphorylation, with oxygen as the terminal electron acceptor and yielding carbon dioxide ($CO_2$) and water as by-products, or anaerobically during glycolysis. While glycolysis can provide energy to cells, the supply is limited because the cellular environment becomes acidic, injuring the cell and inhibiting ATP production.

The vascular circulatory system delivers a continuous supply of energy that is derived from oxygen and nutrients. In the vasculature, a barrier of endothelial cells separates the cells being fed from the vessel lumen. To reach cells outside of the vasculature, oxygen and nutrients must pass through the endothelial lining into the interstitial space. The flow of blood, and thus the flow of nutrients and oxygen can be cut off or reduced as a result of disease or trauma. For example, myocardial infarction (heart attack), stroke, hypotension and severe trauma, such as severing a carotid artery in an automobile accident, result in loss of oxygen, leading to the loss of homeostasis, and possibly resulting in death.

When blood supply is re-established after an ischemic event, an event that results in the loss of oxygen and nutrients to tissue, ischemia-reperfusion injury can occur. As the cells attempt to synthesize ATP, after reoxygenation, toxic metabolites are produced, such as free radicals. Ischemia is not only an injury- or disease-related phenomenon, but can be induced as a side effect of surgeries, such as aortic bypass, open heart surgery, major tissue reconstruction, tumor removal, intestinal resection and organ transplantation.

Ischemia represents an enormous challenge to successful tissue and organ transplantation. About 14,000 kidneys and 2500 hearts are transplanted in the United States each year. After removal, organs have a limited life span in the absence of nutrients and oxygen. Hearts must be transplanted within 4 to 6 hours after harvest, while kidneys must be transplanted within 72 hours. Because recipients are often far from donors, these short viability times hamper transplantation. Blood can be stored for about only 45 days at 4° C. and then must be discarded. More complicated is the acquisition of autologous blood in anticipation of surgery. Patients can usually only provide two units of blood in the 45 days. This amount does not suffice, because many surgical procedures use three, four or more units of blood.

Several attempts have been made to overcome or inhibit the detrimental effects of low oxygen supplies. These approaches include: (1) providing glycolytic intermediates to augment anaerobic ATP production; (2) reducing metabolic demand, such as storing cells, tissues and organs at 4° C.; and (3) adding ATP directly to the cells, tissues or organs. Supplying energy to cells would be preferably accomplished by direct administration of ATP; however, cells take up exogenous ATP poorly because they lack ATP receptors or channels. Furthermore, cell plasma membranes are hydrophobic, while ATP is hydrophilic, preventing the ATP from passing through. Introducing ATP into the blood stream is ineffective because ATP cannot cross the endothelial barrier, and ATP is prone to hydrolysis. In addition, ATP is a purinergic receptor agonist and when administered intravenously, ATP can result in vasodilation and hypotension. Attempts to use liposomes to deliver ATP have been largely unsuccessful and inefficient (Arakawa et al. 1998, Puisieux et al. 1994). For example, Puisieux et al. constructed phosphatidyl choline, cholesterol and phosphatidyl serine lipid vesicles that encapsulated ATP, then incubated the vesicles with sperm cells, liver and brain tissue. Although some uptake was observed, controlled delivery matching metabolic demand for ATP was not achieved. When administered in the blood stream, liposomes are usually unable to breach the endothelial cell barrier; in addition, they usually do not have high rates of fusion with cellular membranes, a necessary event for the vesicle to deliver its ATP payload into the cells.

Animal cell plasma membranes contain four major phospholipids that represent greater than half of the total lipid: phosphatidylcholine, phosphatidylethanolamine, phosphatidylserine and sphingomyelin. Phosphatidylcholine and sphingomyelin are found mostly in the outer leaflet, while phosphatidylethanolamine and phosphatidylserine are found principally in the inner leaflet. Phosphatidylcholine is the most abundant phospholipids found in animal cells. Thus, any liposomal delivery system should be composed primarily of this phospholipids. Furthermore, phosphatidylcholine is the only naturally occurring phospholipids that forms closed lipid vesicles, which protects the intravesicular contents and reduces leakage. Plasma membranes help maintain cellular integrity and are selectively permeable. While some molecules are able to diffuse through membranes, most, including ATP, require other means to enter, such as transport proteins or channels.

Therefore, there continues to be a need for new approaches to deliver biomolecules to cells for a variety of applications, including but not limited to providing biomolecules, such as ATP, to cells and tissues not receiving sufficient quantities of the biomolecules to meet metabolic demand.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides a vesicle, comprising a phospholipid which is stable vesicle former, and at least one unstable vesicle forming member, wherein the unstable vesicle forming member is selected from the group consisting of a polar lipid which is not a stable vesicle former, a PEG, a raft former and a fusion protein. The phospholipid which is stable vesicle former or the polar lipid which is not a stable vesicle former can have the structure of formula (I)

   (I)

wherein X is H, A, or has a structure of formula (II)

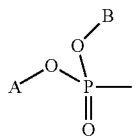   (II)

B is a cation or an alkyl group,
A is a H or an alkyl group,
L is an alkyl further missing two hydrogen atoms, and
each Z is independently H, E, or the structure of formula (XI),

   (XI)

wherein E is an alkyl or alkenyl, and when one Z is H, the other Z is not H.

In some embodiments of the presently disclosed vesicle, A is H, or has a structure selected from the group consisting of formulas (III), (IV), (V), (VI) and (VII)

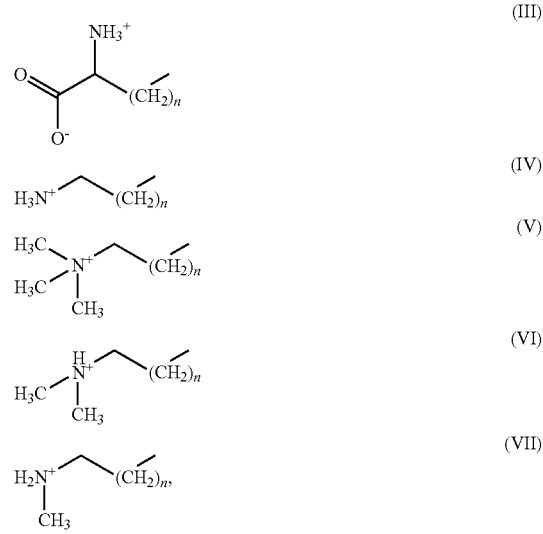

wherein n is an integer from 0 to 4;
L has a structure selected from the group consisting of formulas (VIII), (IX) or (X)

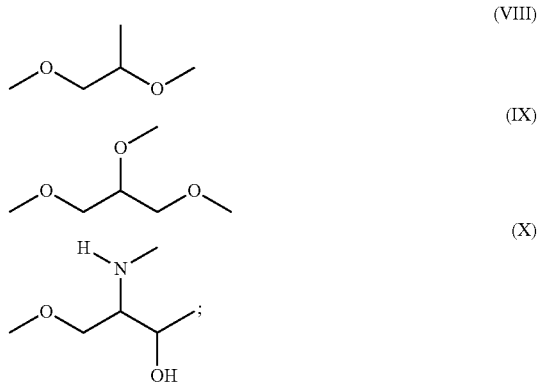

and
E has a structure selected from the group consisting of (XII), (XIII), (XIV), (XV) (XVI), (XVII), (XVIII), (XIX), (XX), (XXI), or (XXII)

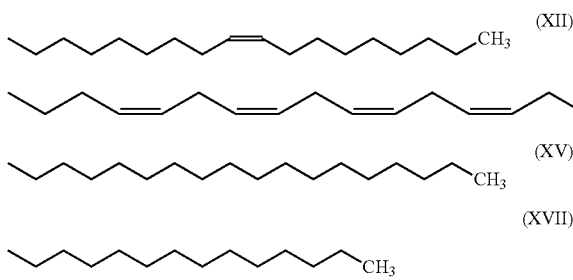

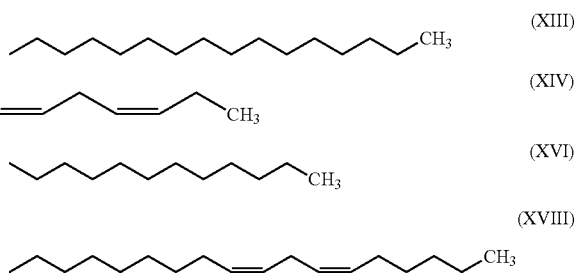

-continued

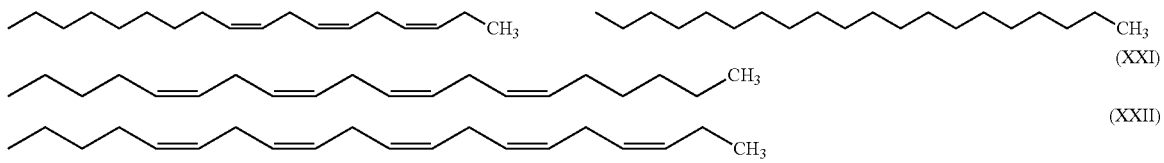

Further, in some embodiments, E can be a bacterial fatty acid. Exemplary bacterial fatty acids include, but are not limited to iso-branched fatty acids, anteiso-branched fatty acids, 15-methyl fatty acids, trans-unsaturated or cis-unsaturated fatty acids, a-hydroxyl fatty acids, b-hydroxyl fatty acids, a-hydroxyl-b-methyl fatty acids, a,b-dihydroxyl fatty acids, cyclohexyl fatty acids, (Z,Z)-unsaturated fatty acids, a-hydroxyl-(bE)-ene, and 2-hexylcyclopropanedecanoic acid.

In some embodiments of the vesicle, the phospholipid which is a stable vesicle former is a phosphatidylcholine, and in some embodiments, the phosphatidylcholine is soy phosphatidylcholine, egg phosphatidylcholine, E. coli extract phosphatidylcholine, 1,2-dioleoyl-sn-glycero-3-phosphocholine (DOPC), 1-palmitoyl-2-docosahexaenoyl-sn-glycero-3-phosphocholine (PDPC), dimyristoyl phosphatidylcholine (DMPC), dipalmitoyl phosphatidylcholine (DPPC), distearoyl phosphatidylcholine (DSPC) or a mixture thereof. Further, in some embodiments, the unstable vesicle forming member is an unstable vesicle forming polar lipid having a structure selected from the group consisting of formulas (XXIV), (XXV), (XXVI), (XXVII), (XXIX), (XXXI), (XXXII), (XXXIII), and (XXXIV). In other embodiments, the unstable vesicle forming member is a PEG having a weight of from about 20 to about 8000 repeat units, a weight of from about 3000 to about 4000 repeat units, or a weight of about 3350 repeat units. Still further, in some embodiments, the unstable vesicle forming member is a raft former selected from the group consisting of cholesterol and sphingomyelin or the unstable vesicle forming member is a fusion protein selected from the group consisting of fertilin, soluble N-ethylmaleimide-sensitive factor attachment protein receptors (SNAREs), sec1/munc18 (SM) polypeptides, viral envelope fusion proteins, and annexins. In some embodiments, the vesicle comprises two or more of the unstable vesicle forming members.

In some embodiments of the vesicle, the vesicle further comprises a biomolecule. In some embodiments, the biomolecule is a lipid-soluble biomolecule, which can be selected from the group consisting of α-tocopherol (Vitamin E), retinol (Vitamin A), phyllochinon (Vitamin K), ergocalciferol (Vitamin D), cholesterol, cholesterol esters, steroids, hopanoids, detergents, fatty acids, bacterial branched fatty acids, isoprenoids, long chain alcohols, lipid-soluble anesthetics, gangliosides, lipopolysaccharides, biotin-labeled phospholipids, membrane ion conductance channels, transport proteins, glucose transporters, adhesion proteins, gap junction proteins, synaptic junction proteins, caspases, adherence proteins, G-proteins, MHC proteins, complement proteins, lipid-soluble viral proteins, cellular receptors, lipid-soluble fluorescent probe molecules, and lipid-soluble radioactive tracer molecules. In some embodiments, the biomolecule is a water-soluble biomolecule, which can be selected from the group consisting of amino acids, polypeptides, proteins, monosaccharides, disaccharides, polysaccharides, nucleotides, polynucleotides, water-soluble vitamins, minerals, high energy phosphates, glycolytic, oxidative intermediates, nicotinadenine dinucleotide (NAD+ or NADH), flavin adenine dinucleotide (FAD+ or FADH2), water-soluble cellular enzymes, insulin, water-soluble fluorescent probe molecules, water-soluble radioactive tracer molecules, and water-soluble drugs. Further, in some embodiments, the biomolecule is a high-energy phosphate selected from the group consisting of ATP, ADP, AMP, adenosine, CTP, CDP, CMP, cytosine, UTP, UDP, UMP, uracil, GTP, GDP, GMP, guanosine, TTP, TDP, TMP, thymine, ITP, IDP, IMP, and inosine.

In some embodiments, the presently disclosed subject matter provides a vesicle, comprising a biomolecule (such as for example ATP), soy phosphatidylcholine, and DOTAP. In some embodiments, the ATP is present at a concentration of from about 0.01 mM to about 200 mM. Further, in some embodiments, the vesicle has a ratio of soy phosphatidylcholine to DOTAP of about 50:1.

In some embodiments, the presently disclosed subject matter provides a vesicle, comprising a biomolecule (such as for example ATP), DOPC, and DOTAP. In some embodiments, the ATP is present at a concentration of from about 0.01 mM to about 200 mM. Further, in some embodiments, the vesicle has a ratio of soy phosphatidylcholine to DOTAP of about 50:1.

In some embodiments, the presently disclosed subject matter provides a method of delivering a biomolecule to a cell, comprising contacting the cell with a vesicle of the presently disclosed subject matter. In some embodiments, the vesicle further comprises a biomolecule, which in some embodiments is ATP. Further, in some embodiments, an amount of ATP delivered to the cell by the vesicle is sufficient to offset the ATP utilization events and help maintain the cell during periods of low oxygen or nutrients.

In some embodiments, the presently disclosed subject matter provides a method for treating a wound, comprising contacting the wound with a composition comprising a vesicle of the presently disclosed subject matter, which comprises a biomolecule. In some embodiments, the biomolecule is ATP. In some embodiments, the vesicle further comprises becaplermin, fibroblast growth factor, vascular endothelial growth factor, an antibiotic, silver containing compositions, a skin graft composition or combinations thereof.

In some embodiments, the presently disclosed subject matter provides a method of improving the productivity of a bioreactor having at least one cell, comprising contacting the cell with a vesicle. The vesicle can comprise a biomolecule, which in some embodiments is ATP.

In some embodiments, the presently disclosed subject matter provides a method for preserving tissue, comprising contacting tissue with a vesicle of the presently disclosed subject matter. The vesicle can comprise a biomolecule. In some embodiments, the biomolecule is ATP.

Accordingly, it is an object of the presently disclosed subject matter to provide lipid vesicles for the delivery of biomolecules to cells and methods for using the same. This object and other objects are achieved in whole or in part by the presently disclosed subject matter.

An object of the presently disclosed subject matter having been stated above, other objects will become evident as the description proceeds, when taken in connection with the Examples and Figures as described hereinbelow.

BRIEF DESCRIPTION OF THE DRAWINGS

FIG. 6A is a photomicrograph after 14 days following perfusion with biotinylated vesicles and fluorescent Streptavidin. FIG. 6B is a photomicrograph of non-biotinylated vesicles and fluorescent Streptavidin. Magnification of 100× for both FIGS. 6A and 6B.

DETAILED DESCRIPTION

Figure 1:
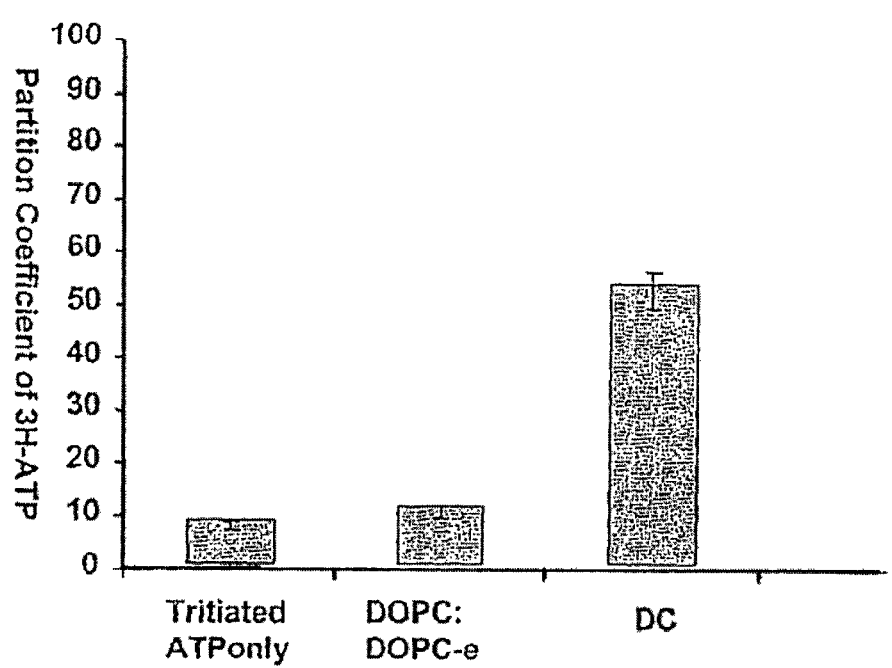
FIG. 1 is a bar graph showing the partition coefficient of ATP within human umbilical vein endothelial cells (HUVEC) after one hour.

The present subject matter makes use of the discovery that small lipid vesicles that are absorptively compatible with cellular bilipid membranes can encapsulate biomolecules and deliver the biomolecules directly to cells. The rate of biomolecule delivery can be controlled by varying the lipid vesicle composition, as well as by other means, resulting in different absorption rates. In addition, the vesicle composition can be modulated to accommodate different modes of administration. For example, small lipid vesicles can be made such that when injected into the circulation, the vesicles can bypass endothelial cells, opening up gaps so that they can absorb efficiently with the target cells. To encourage or target absorption, other components can be added to the vesicles, such as certain polypeptides. By being loaded into a lipid vesicle, biomolecules can be stabilized against hydrolysis.

The compositions and methods of the presently disclosed subject matter meet the requirements for effective biomolecule delivery to cells, including for example ATP delivery to cells. Four goals of effective delivery of biomolecules to cells are: First, the biomolecules must pass through or into the cell membrane, depending on the biomolecule being delivered. Second, the amount of biomolecules must be delivered at a rate that can help offset the basal metabolic demand of the cell for the biomolecule, such as for example the metabolic demands of cells under a variety of conditions for ATP. Third, the biomolecule-containing composition must be compatible with the route of administration. Finally, to be effective, the biomolecule must enter the cells or cell membranes before degradation of the biomolecule.

Lipid vesicle membranes resemble plasma cell membranes; in addition, they are simple to make. Because they have an aqueous portion, lipid vesicles can encapsulate various solutions, including those containing biomolecules, such as ATP. However, vesicles also comprise a hydrophobic component and therefore can be utilized to deliver to cells hydrophobic biomolecules as well. Lipid vesicles can be made to absorb with cell membranes, allowing for the delivery of the lipid vesicles' contents.

The methods and compositions of the subject matter disclosed herein have a large array of uses, including treating hemorrhagic shock, heart attack, coronary heart disease, stroke, hypotension, severe trauma, wound healing, tissue and organ storage, cardiopulmonary resuscitation, and transplantation. In the case of severe trauma, the compositions of the presently disclosed subject matter can be administered in the field to minimize damage until medical help is available. The methods and compositions can also be used to prolong blood and platelet storage.

Throughout the specification and claims, a given chemical formula or name shall encompass all optical and stereoisomers as well as racemic mixtures where such isomers and mixtures exist.

The following, not meant to limit the presently disclosed subject matter, is presented to aid the practitioner, although other methods, techniques, cells, reagents and approaches can be used.

DEFINITIONS

"Alkyl" (or alkyl- or alk-) refers to a substituted or unsubstituted, straight, branched or cyclic hydrocarbon chain, preferably containing of from 1 to 20 carbon atoms. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, cyclohexyl, and the like. There can be optionally inserted along the alkyl chain one or more oxygen, sulfur or substituted or unsubstituted nitrogen atoms. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon chain that contains at least one double bond, and preferably 2 to 22 carbon atoms. Exemplary unsubstituted alkenyl groups include ethenyl (or vinyl), 1-propenyl, 2-propenyl (or allyl) 1,3-butadienyl, hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkoxy" refers to a substituted or unsubstituted, -0-alkyl group. Exemplary alkoxy groups include methoxy, ethoxy, n-propoxy, isopropoxy, n-butoxy, t-butoxy, and the like.

"Aryl" refers to any monovalent aromatic carbocyclic or heteroaromatic group, preferably of 3 to 10 carbon atoms. The aryl group can be bicyclic (i.e. phenyl (or Ph)) or polycyclic (i.e. naphthyl) and can be unsubstituted or substituted. Preferred aryl groups include phenyl, naphthyl, furyl, thienyl, pyridyl, indolyl, quinolinyl or isoquinolinyl.

"Amino" refers to an unsubstituted or substituted —NRR' group. The amine can be primary (—NH$_2$), secondary (—NHR) or tertiary (—NRR'), depending on the number of substituents (R or R'). Examples of substituted amino groups include methylamino, dimethylamino, ethylamino, diethylamino, 2-propylamino, 1-propylamino, di(n-propyl)amino, di(iso-propyl)amino, methyl-n-propylamino, t-butylamino, anilino, and the like.

The term "quaternary nitrogen" refers to a nitrogen atom that participates in either four single bonds, two single bonds and one double bond, one single bond and one triple bond, or two double bonds. Thus, in some embodiments of the presently disclosed subject matter, the term "quaternary nitrogen" refers to a nitrogen atom substituted with four substituent groups, including one group that further serves to attach the quaternary nitrogen to a linking group "L" or an oxygen atom of a compound of formula (II) as disclosed herein. Thus, in some embodiments, the quaternary nitrogen has the following structure:

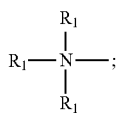

wherein each $R_1$ is independently selected from the group consisting of H, alkyl, substituted alkyl, branched alkyl, cycloalkyl, alkenyl, hydroxyalkyl, alkoxyalkyl, aryl, substituted aryl, and aralkyl.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with a substituent. The ring can be mono-, bi- or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzthiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Substituted" means that the moiety contains at least one, preferably 1-3 substituent (s). Suitable substituents include hydrogen (H) and hydroxyl (—OH), amino (—NH2), oxy (—O—), carbonyl (—CO—), thiol, alkyl, alkenyl, alkynyl, alkoxy, halo, nitrile, nitro, aryl and heterocyclic groups. These substituents can optionally be further substituted with 1-3 substituents. Examples of substituted substituents include carboxamide, alkylmercapto, alkylsulphonyl, alkylamino, dialkylamino, quaternary nitrogen, carboxylate, alkoxycarbonyl, alkylaryl, aralkyl, alkylheterocyclic, and the like.

Lipid Vesicles

Lipid vesicles resemble plasma membranes, and they can be made to absorb with cell membranes. Previous liposome studies have shown that four major types of interactions are observed between liposomes and cell membranes: adsorption to cell surface; endocytosis (the active taking-up of the liposome by phagocytic cells); lipid exchange (involving the transfer of individual lipid molecules between the liposome and the plasma membrane); and fusion (where the liposome membranes unite with plasma cell membranes). "Absorb", "absorption", and "absorptive", as the terms are used herein encompass all of the interactions between liposomes and cell membranes, including adsorption, endocytosis, lipid exchange, and fusion.

Fusion provides a mechanism of interest since it allows for the direct introduction of vesicular contents into the cell. Absorption or lipid exchange is also of interest, particularly when delivery of lipid-soluble biomolecules to target cells is desired. Endocytosis can occur in certain types of cells, such as leukocytes, and can also be a mechanism of absorption of the vesicle with target cells.

Most liposomes and multilamellar vesicles are not readily fusogenic, mainly because the stored energy of the vesicle radius of curvature is minimal. However, the small unilamellar vesicles of the presently disclosed subject matter, which have a very tight radius of curvature, can be engineered to be very absorptive, including fusogenic in some embodiments. The average hydrodynamic diameter of a small unilamellar vesicle (SUV) of the presently disclosed subject matter is in some embodiments about 20 nm to about 600 nm; in some embodiments about 100 nm to about 300 nm; and in other embodiments about 10 nm to about 100 nm, more preferably about 20 nm to about 60 nm, including about 40 nm. This size allows vesicles to pass through the gaps between endothelial cells. Useful vesicles of the presently disclosed subject matter may vary greatly in size and are selected according to a specific application and desired mechanism of delivery (e.g., fusion, lipid exchange, endocytosis, etc.) to a target cell.

The compositions from which the presently disclosed vesicles are formed can contain a polar phospholipid which is a stable vesicle former, preferably together with at least one unstable vesicle forming member, which can be selected from the group consisting of polar lipids which are not stable vesicle formers, PEGs, raft formers, and/or fusion proteins.

Polar lipids, including the phospholipid stable vesicle formers and, in some embodiments, the polar lipids which are not stable vesicle formers, are organic molecules which have a hydrophobic end and a hydrophilic end, and contain at least six carbon atoms. They can have the structure of formula (I)

 (I), where X is a head group, L is a back bone group, and each Z is a fatty group. The two Z groups can be the same or different.

A phospholipid is a polar lipid, which has a head group comprising a phospholipid. The presently disclosed subject matter includes phospholipids encompassed by compositions having a head group of formula (II), where A and B are substituents of the head group.

The head group, X, of polar lipids encompassed by the presently disclosed subject matter, including for example stable vesicle forming lipids and lipids that are not stable vesicle formers, can be any polar group, preferably a cationic, anionic or zwitterionic group, or H. In some embodiments, X is a group of formula (II). In other embodiments, X is A. A can be H, or an alkyl group. In some embodiments, A is an alkyl group substituted with an amine, and in some embodiments A is a group of formula (III), (IV), (V), (VI) or (VII), wherein n is an integer from 0 to 4. B can be a cation, such as Na$^+$, K$^+$, or tetramethyl ammonium ion, or an alkyl group.

It should be noted that throughout the specification, the formulas may show the structures in protonated form, but that they also include the unprotonated form (and vice versa);

which form is present in any composition will depend on the exact pH of the composition, and the presence of water and/or appropriate counter ions.

The back bone group, L, can be an alkyl further missing two hydrogen atoms (to give a total of three open attachment points), and can be in some embodiments an alkoxy, or amino substituted alkyl. In particular embodiments, L is a group of formula (VIII), (IX) or (X).

The fatty groups, Z, can be the same or different, and in some embodiments are H, an E group, or the structure of formula (XI), where E is an alkyl or alkenyl. In some embodiments, E is an unsubstituted straight chain alkyl or alkenyl, with 6-26 carbon atoms. In particular embodiments, E is a group of formula (XII), (XIII), (XIV), (XV) (XVI), (XVII), (XVIII), (XIX), (XX), (XXI), or (XXII). In other particular embodiments, E is a bacterial fatty acid. Exemplary bacterial fatty acids include, but are not limited to iso-branched fatty acids, anteiso-branched fatty acids, 15-methyl fatty acids, trans-unsaturated or cis-unsaturated fatty acids, a-hydroxyl fatty acids, b-hydroxyl fatty acids, a-hydroxyl-b-methyl fatty acids, a,b-dihydroxyl fatty acids, cyclohexyl fatty acids, (Z,Z)-unsaturated fatty acids, a-hydroxyl-(bE)-ene, and 2-hexylcyclopropanedecanoic acid. If one of the fatty groups is H, then the other is different. If double bonds are present, then the cis configuration is preferable in particular embodiments.

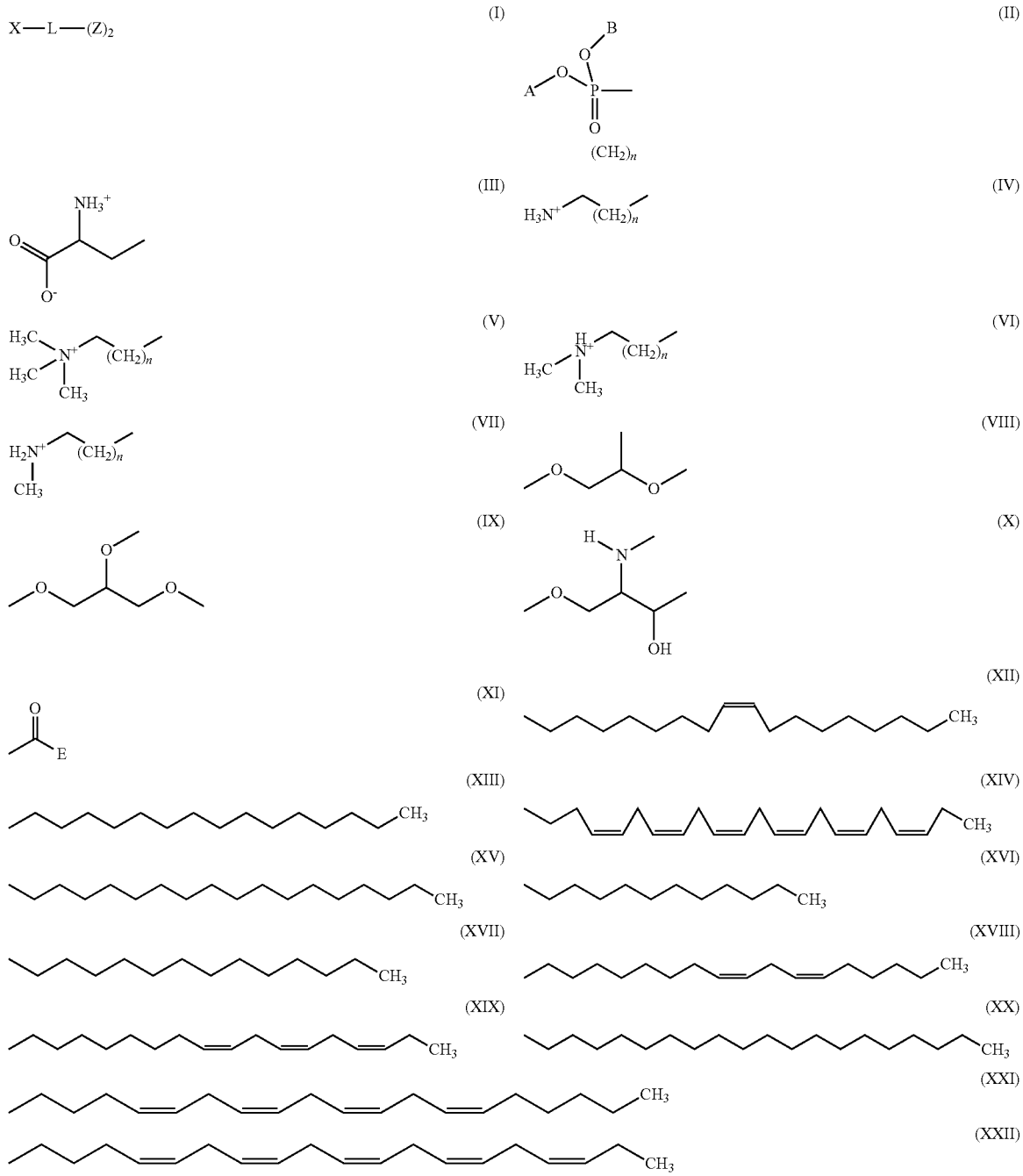

A phospholipid (or polar lipid) which is a stable vesicle former is a phospholipid (or polar lipid) that will form vesicles, at least 50% of which persist for at least one hour, when prepared as follows: the phospholipid is dissolved in chloroform and placed in glass test tube. Solvent is removed by evaporation under a steady stream of nitrogen gas, followed by solvent removal by subjecting the sample to vacuum for twelve hours. The dried lipid material is then re-hydrated in 10 mM $Na_2HPO_4$, for 60 minutes at a temperature above the lipid phase transition temperature; the desired final concentration is 25 mg/ml. The lipid mixture is then agitated by sonication with a microtip 450 watt sonicator used at a 40% duty cycle. In some instances it is also preferable to use high-pressure homogenization and/or high-pressure extrusion through fixed-diameter filters.

Examples of polar lipids that are suitable for use as stable vesicle forming members include, but are not limited to 1,2-dioleoyl-sn-glycero-3-phosphocholine (DOPC) (formula XXIII), 1-palmitoyl-2-docosahexaenoyl-sn-glycero-3-phosphocholine (PDPC) (formula XXVIII), dimyristoyl phosphatidylcholine (DMPC) dipalmitoyl phosphatidylcholine (DPPC), distearoyl phosphatidylcholine (DSPC), soy phosphatidylcholine (soy PC), egg phosphatidylcholine, E. coli extract phosphatidylcholine or a mixture thereof.

Figure 4:
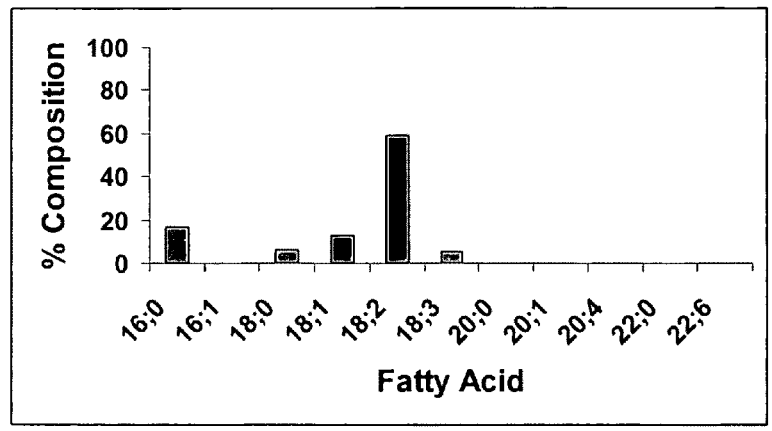
FIG. 4 is a graph showing the fatty acid composition of soy phosphatidylcholine (PC) as determined by GC/MS. Soy PC has a very low saturated/unsaturated ratio (0.3), which indicates a preponderance of unsaturated lipids, which can increase fusion.

In some embodiments of the presently disclosed subject matter, the stable vesicle forming polar lipid can be derived from a natural source, such as for example from the extraction of natural lipids from plants, animals, yeast, and bacteria. Extraction of polar lipids from natural sources can provide suitable lipids as well as cost-saving benefits. For example, polar lipids useful with the presently disclosed subject matter can be derived from soybean sources. Soybean oil is a large bulk commodity of the food industry, and is used for the extraction of soybean lecithin (soy PC). Varying degrees of purity of soy PC are available from 30%-100%. Soy PC has a preponderance of diunsaturated linoleic acid, and mixed chain (e.g., sn-1 saturated and sn-2 unsaturated), which can increase the absorptive potential of this natural lipid extract. See FIG. 4. The major "contaminants" of soy PC are lysophosphatidylcholine (lyso PC) and free fatty acids, which are by-products of the extraction and refinement process. Interestingly, both lyso PC and free fatty acids can act to facilitate absorption of the vesicle with a target cell. Therefore, in some embodiments of the presently disclosed subject matter, a vesicle can comprise, for example, 95% soy PC as the stable vesicle former and 5% lyso PC and the free fatty acids act as unstable vesicle forming members. This formulation decreases the amount of other unstable vesicle forming members, such as for example DOTAP or POPA, necessary to achieve the same desired absorption rate. Thus, this formulation may or may not require the addition of other unstable vesicle forming members, depending on the desired absorption rate.

In addition to the above-noted advantages of soy PC in particular, the natural extraction of lipids from animals, plants, yeast and bacteria can be used as a recycling source for the lipids used in the production of vesicles of the presently disclosed subject matter. As a non-limiting example, a bioreactor using E. coli for the production of insulin can be used as a source of lipid material (from the E. coli) for the stable forming lipid in liposomes of the presently disclosed subject matter. In this manner, the amount of lipid material needed for large batches is reduced, thereby decreasing costs.

In some embodiments, in addition to the phospholipid which is a stable vesicle former, at least one other polar lipid is included, such as for example one or more polar lipids which are not stable vesicle formers.

Examples of polar lipids for use in the present subject matter as unstable vesicle forming members include, but are not limited to 1-palmitoyl-2-oleoyl-sn-glycero-3-phosphate (POPA) (formula XXIV), 1,2-dioleoyl-sn-glycero-3-ethylphosphocholine (DOPC-e) (formula XXV), 1,2-dioleoyl-sn-glycero-3-phosphoethanolamine (DOPE) (formula) (XVI), 1,2-dioleoyl-sn-glycero-3-[phospho-1-serine] (DOPS) (formula XXVII), a typical sphingomyelin (e.g., formula XXIX) (cholesterol (formula XXX) will form rafts when added to a vesicle formed from a mixture of a sphingomyelin and DOPC), 1,2-dimyristoyl-sn-glycerol (formula XXXI), 1-palmitoyl-2-hydroxy-sn-glycero-3-phosphocholine (XXXII), 1,2-dioleoyl-3-trimethylammonium-propane (DOTAP) (formula XXXIII), and 1,2-dioleoyl-3-dimethylammonium-propane (DODAP)(formula XXXIV).

Other polar lipids useful for the practice of the presently disclosed subject matter as unstable vesicle forming members include phosphatidyl serine (PS), phosphatidyl glycerol (PG), mixed chain phosphatidyl choline (MPC), phosphatidyl ethanol (PE), and phospholipids containing docosahexaenoic acids. Cit-DOPC and cit-DOPC-e are examples of polar lipids useful as unstable vesicle forming members. Phosphatidylcholines, including those having a docosahexaenoic acid in the sn-1 and sn-2 positions (DHPC) may be used. Other diunsaturated lipids, such as diarachidonylphosphatidylcholine (for example 20:4 DOPC:DArPC), dilinolenoylphosphatidylcholine (for example 18:3 DOPC:DLnPC) are also useful. For example, DOPC may be mixed with increasing amounts of DLnPC, DArPC and DHPC during vesicle preparation. Useful ratios include (DOPC:DLnPC, DArPC or DHPC) ranging from 1-1000:1, such as for example 25-500:1, including 1:1, 25:1, 50:1, 100:1, 500:1, and 1000:1. Combinations of phospholipids having large mean molecular areas can also be used, such as DOPC:DLnPC:DHPC. Diacylglycerol, a non-lamellar phase lipid, can also be mixed with DOPC.

In some embodiments, the unstable vesicle forming member is a DOTAP and/or a DODAP. DOTAPs and DODAPs are modified lipids that carry a net positive charge at physiological pH. The interaction of DOTAPs and DODAPs with negatively charged species is complex. However, and without wishing to be limited by theory, a possible mechanism of intracellular delivery when DOTAPs and/or DODAPs are utilized as unstable vesicle forming members in vesicle compositions of the presently disclosed subject matter is by passive entry via increased membrane permeability. When DOTAPs and/or DODAPs are added to a phosphatidylcholine lipid vesicle, for example, the DOTAPs and/or DODAPs can be used as complexing agents to negatively charged species, and also, as a means to increase surface charge density on the lipid vesicle. Increased surface charge can be an important factor in membrane absorption events. In addition, DOTAPs and DODAPs have head groups which occupy less space and thus can induce packing constraint issues when placed in a phosphatidylcholine vesicle, for example.

It is interesting to note that lipid vesicles which are composed of DOTAPs and/or DODAPs may well have more than one mechanism responsible for the intracellular delivery of negatively charged agents. For example, DOTAPs and DODAPs may increase absorption of lipid vesicles to cells, allowing for intracellular contents delivery, or alternatively, the DOTAPs and/or DODAPs can bind negatively charged species and assist in the amount of the negatively charged species that is found in the cell plasma membrane (i.e., the absorption of the DOTAPs and/or DODAPs into the plasma membrane may result in the deposition of substances in the membrane, both outer and inner leaflet). DOTAPs and DODAPs are also produced commercially and therefore are readily available. They have also been used in GMP processes.

Figure 5:
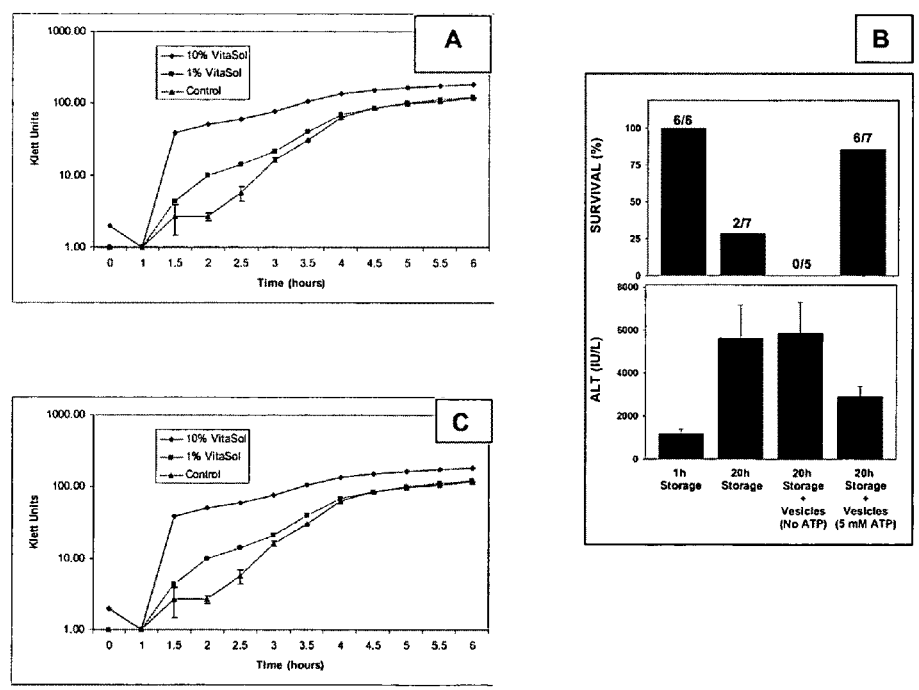
FIGS. 5A-5C are graphs showing a vesicle comprising soy PC/DOTAP (50:1) increases bacterial growth rates (FIG. 5A) and also helps maintain liver preservation (FIGS. 5B and 5C).

Thus, DOTAPs and DODAPs are well-suited examples of unstable vesicle forming members in the vesicles of the presently disclosed subject matter. In particular embodiments, the vesicles comprise soy PC/DOTAP (50:1 mol/mol). In other particular embodiments, the vesicles comprise DOPC/DOTAP (50:1 mol/mol). Further, in some embodiments the vesicles comprise ATP (e.g., at a concentration of 10 mM). These formulations have been used in liver preservation applications. This combination of lipids resulted in a significant maintenance of hepatic ATP levels and also maintained liver preservation over extended ex vivo storage times (FIGS. 5B and 5C). Further, these formulations have been used successfully in increasing bacterial growth rates (FIG. 5A).

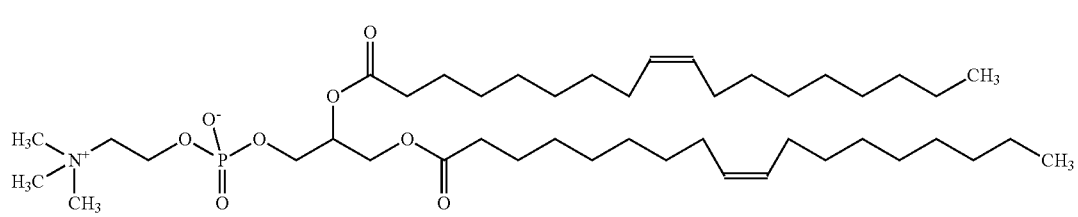
(XXIII)

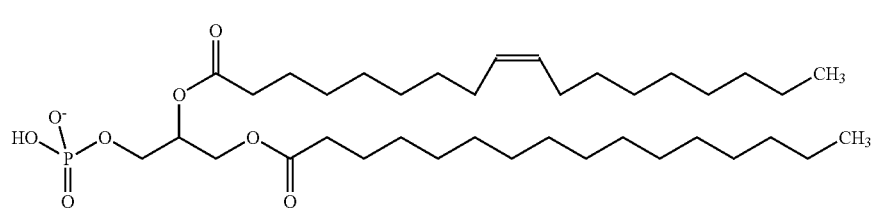
(XXIV)

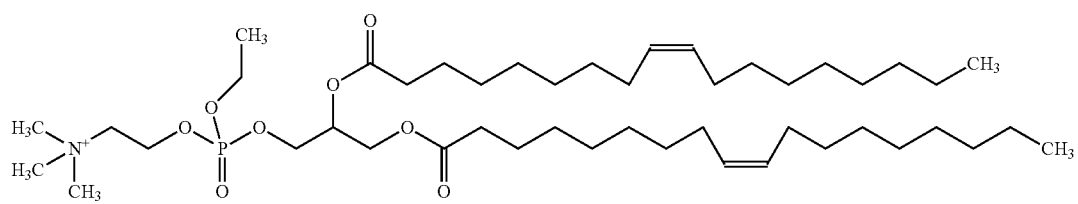
(XXV)

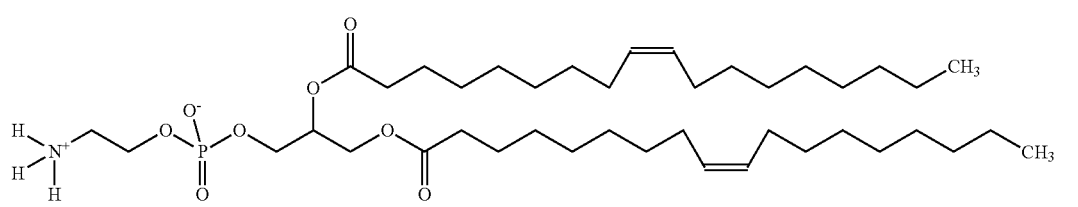
(XXVI)

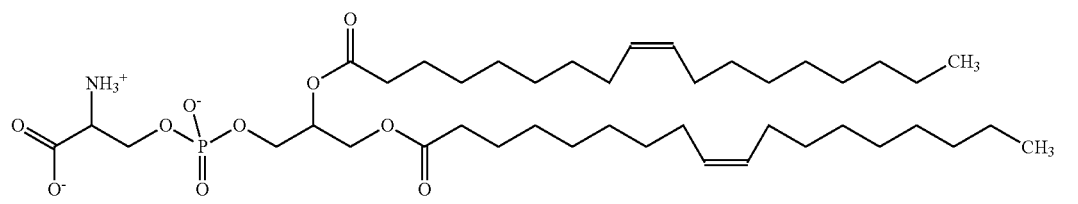
(XXVII)

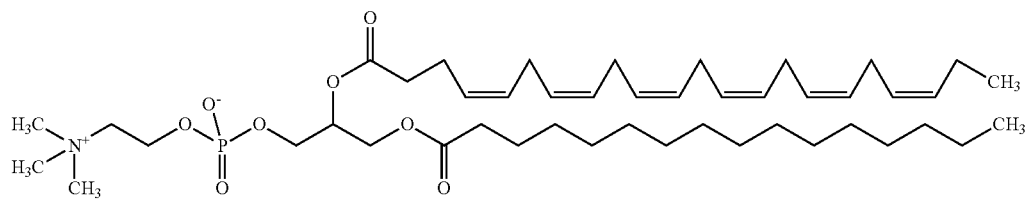
(XXVIII)

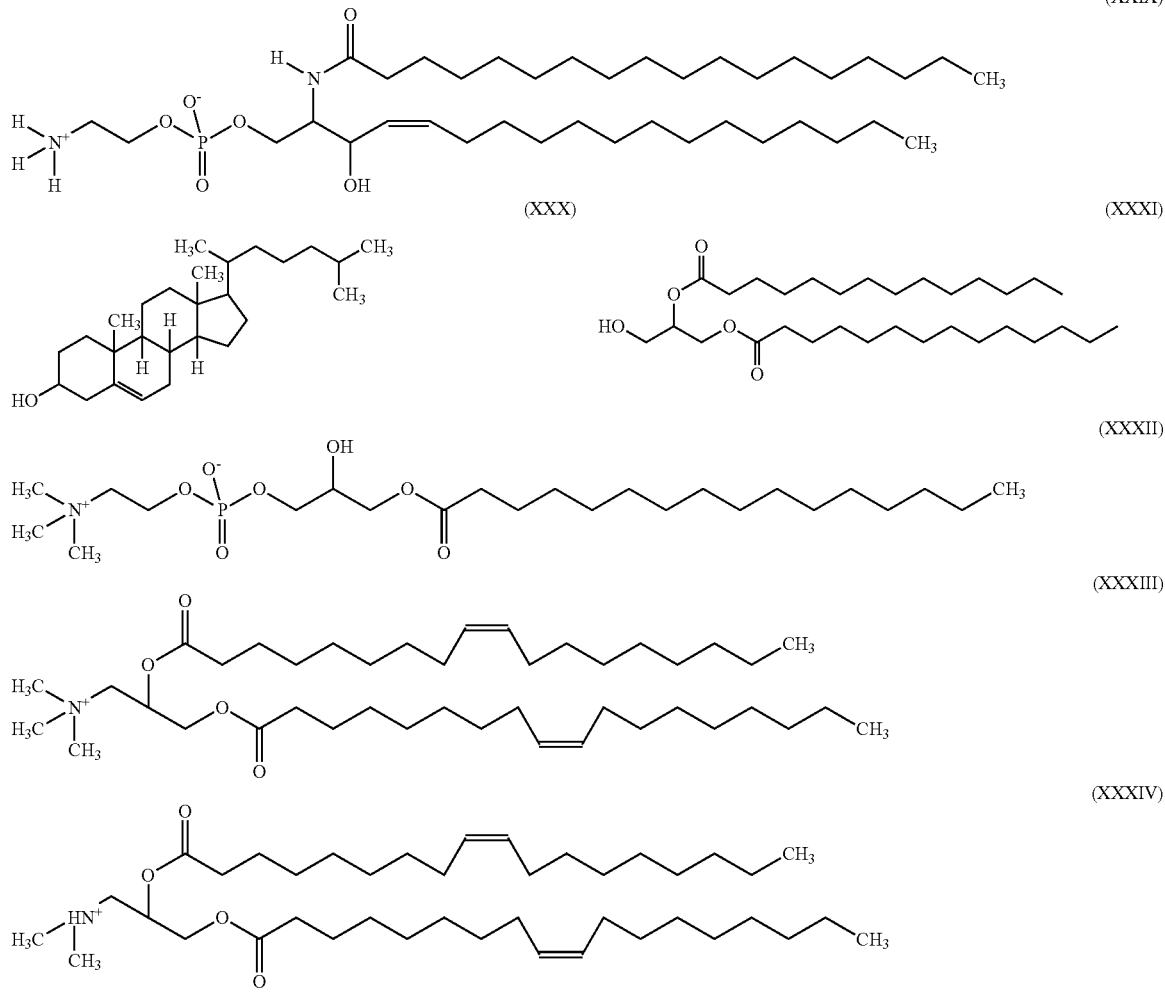

A raft former can also be utilized as an unstable vesicle forming member in the vesicles of the presently disclosed subject matter. A raft former is a compound which will form or cause formation of discrete regions containing the raft forming compound within the membrane bilayer. These discrete regions tend to destabilize the vesicle, increasing its absorptivity, e.g., its fusogenicity. Examples of raft formers are cholesterol (formula XXX), sphingomyelin, and proteins and polypeptides know to be membrane bound. Absorptivity may also be enhanced by selecting polar lipids, which will result in a surface charge on the vesicle, which is the opposite of the charge of the Gouey-Chapman layer of the target cells (typically the Gouey-Chapman layer is positively charged).

In some embodiments, one or more fusion proteins, i.e., polypeptides involved in membrane fusion, can be utilized as unstable vesicle forming members to manipulate the absorption rates of vesicles. Non-limiting examples of fusion proteins useful for incorporation in vesicles of the presently disclosed subject matter include polypeptides that are involved in membrane fusion, such as fertilin, soluble N-ethylmaleimide-sensitive factor attachment protein receptors (SNAREs), SM (sec1/munc18) polypeptides (such as mammalian isoforms of Vps33p, Sly1p and Vps45p; (Jahn and Sudhof 1999) and viral envelope fusion proteins, such as those from Human Immunodeficiency Virus (HIV; e.g., gp41), Semiliki Forest virus, and Influenza). The mammalian SNARE family includes the syntaxins (1A, 1B, 1C; 2 (and splicing variants); 3, 3A, 3B, 3C, 3D; 4; 5, 5A, 5B, 6, 7, 8, 10, 11, 12, 13 (may be identical to 12); 16 (A, B, C); and 17), Hsyn 16, rbet1, GS15, GOS32, GOS28, Membrin, the SNAPs (25, 25a, 25b; 23, 23A, 23B; 29), vti1b, Synaptobrevins (1 and splicing variants; 2), Cellubrevin, VAMP4, VAMP5/6, Ti-VAMP, Endobrevin, Tomosyn and msec22b (Jahn and Sudhof 1999). The term "fusion protein" as used herein also refers to amphiphilic peptides that destabilize membranes, even if their primary function is not to mediate membrane fusion, such as for example annexins (Jahn and Sudhof 1999).

To target specific cells, polypeptides that either interact with a polypeptide specific to the targeted cell, such as a ligand-receptor interaction (at least in the area in which the vesicles are administered), or antibodies recognizing cell-specific antigens may be incorporated into vesicles of the presently disclosed subject matter and are also considered "fusion proteins" as the term is used herein. Other targeting polypeptides include those used during intercellular membrane transport and the Rab GTPase proteins. Viral fusion proteins can also be exploited as targeting molecules. Membrane bound substances, such as biotinylated lipids, and carbohydrates may also be used.

In addition, in some embodiments, polyethylene glycol (PEG) can be utilized as an unstable vesicle forming member.

The PEG can in some embodiments have weights of from about 20 up to about 8,000 repeat units, in some embodiments from about 1,000 to about 6,000 repeat units, and in some embodiments from about 3,000 up to about 4,000 repeat units. In a particular embodiment, the PEG has a weight of about 3,350 repeat units. The PEG can be incorporated into the vesicle at the same time as the stable vesicle forming member in some embodiments. For example, the stable vesicle forming member and the PEG are mixed together prior to or during formation of the vesicle.

The ratio of the stable vesicle forming member to the unstable vesicle forming member (stable:unstable) can be in some embodiments 1:9 to 100,000:1, in some embodiments 1:1 to 1,000:1, in some embodiments 1:1 to 500:1, in some embodiments 1:1 to 250:1, more preferably 10:1 to 100:1 (for example, 50:1). Non-limiting examples include: DOPC/DOPC-e (1:1); DOPC/POPA (50:1), DOPC/POPA (1:1), DOPC/DOTAP (50:1), soy PC/DOTAP (50:1), and soy PC/PEG 3350 (1:1).

Lipid Vesicle Construction

To construct lipid vesicles, in one embodiment lipids are dissolved in chloroform or other appropriate organic solvent and placed in a vessel, such as glass test tube. Solvent is removed by evaporation under a steady stream of nitrogen or other inert gas, followed by air removal, such as subjecting the sample to a vacuum for 0.1 to 48 hours, such as 1, 2, 3, 4, 5, 6, 7, 8, 9, 10, 11, 12, 15, 20, 24, 25, 30, 36, 40, 42 or 48 hours. Twelve hours usually suffices. The dried lipid material is then re-hydrated in an appropriate buffer, such as Hank's Balanced Salt Solution (HBSS) or 10 mM $Na_2HPO_4$, for 30-60 minutes at a temperature above the lipid phase transition temperature; the desired final concentration is usually approximately 1 to 30 mg/ml, typically around 10 mg/ml. The lipid mixture is then agitated. For example, sonication can be used; such as a microtip 450 watt sonicator used at a 40% duty cycle to create SUVs. The length of time of sonication depends on the amount of lipid material; in any case, sonication is stopped when no further decreases in percent transmission are observed or the correct vesicle size is achieved by analysis using a particle size analyzer.

In another embodiment, lipid vesicles are constructed by dissolving lipid materials (e.g., base lipids(s) and fusogenic lipid(s)) in an organic solvent and freeze-dried for a time period sufficient to remove the solvent (e.g., overnight). The lipids can then be hydrated with buffer at approximately 45° C. The lipid vesicles are stirred for approximately 1-hour at 45° C. Compounds to be encapsulated into the vesicles, including for example trehalose and Mg-ATP, are added to the solution and the resultant multilamellar vesicles are subjected to high-pressure homogenization above the phase transition temperature of the base lipid. The unilamellar vesicles formed from this step can be additionally processed by high-pressure extrusion. The vesicles prepared in this manner can be immediately freeze-dried for final use.

Dynamic light scattering (DLS) can be implemented to determine the diameter of the emulsified liposomes, and percent encapsulation can be determined by luminescence using a luceferin-based assay, as is generally known in the art. Further, lipids can be analyzed by UV spectroscopy and thin layer chromatography (TLC) to assess the extent of oxidation, if desired.

Other solutions may be used when rehydrating the dried lipids. These include those buffered with N,N-bis(2-hydroxyethyl)-2-aminoethanesulfonic acid (BES), histidine, bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl) methyl-2-aminoethanesulfonic acid (TES), N-tris (hydroxymethyl)methyl-glycine (Tricine), and tris (hydroxymethyl)-aminomethane (Tris). Other examples of suitable solutions include salt solutions, such as Alseverr's Solution, Dulbecco's Phosphate Buffered Saline (DPBS), Earle's Balanced Salt Solution, Gey's Balanced Salt Solution (GBSS), Puck's Saline A, Tyrode's Salt Solution, St. Thomas Solution and University of Wisconsin Solution.

Biomolecule Encapsulation and Delivery

The presently disclosed subject matter discloses lipid vesicles that can be utilized to deliver molecules, such as biological molecules (biomolecules) required by a cell under specified conditions (e.g., metabolic stress) to meet metabolic demands under the specified conditions. Lipid vesicles of the presently disclosed subject matter can absorb with a target cell plasma membrane and deliver a biomolecule carried by the vesicle to the target cell. Since the vesicles of the presently disclosed subject matter comprise both a hydrophobic lipid membrane and an aqueous compartment enclosed by the membrane, the vesicles disclosed herein can deliver two distinct groups of matter; hydrophobic molecules carried in the vesicle membrane and water soluble molecules encapsulated by the vesicles.

Hydrophobic biomolecules carried by the vesicle can be deposited into the target cell plasma membrane and the rate of deposition can be controlled by varying the absorption rate of the vesicles (e.g., size, charge, aggregating agents, dissimilar lipid species) and the concentration of the lipid soluble biomolecule in each vesicle. The membrane solubility for each lipid soluble biomolecule can be determined experimentally by addition of the biomolecule to the target cell bilayer using methods known to those of skill in the art. The amount of each biomolecule that can be delivered per vesicle can be determined by measuring the uptake of the lipid soluble biomolecules into target tissue by radioactive tracing experiments widely available to those of skill in the art. For example, $^3$H-ATP can be encapsulated into the above mentioned lipid vesicle and then added to cells. After a given period of time, the cells are washed several times to remove vesicles which have not been absorbed by the cells. The cells are removed from their dish and then placed in a liquid scintillation fluid and the extent of incorporation of the $^3$H-ATP can be quantified using a beta counter.

Figure 6:
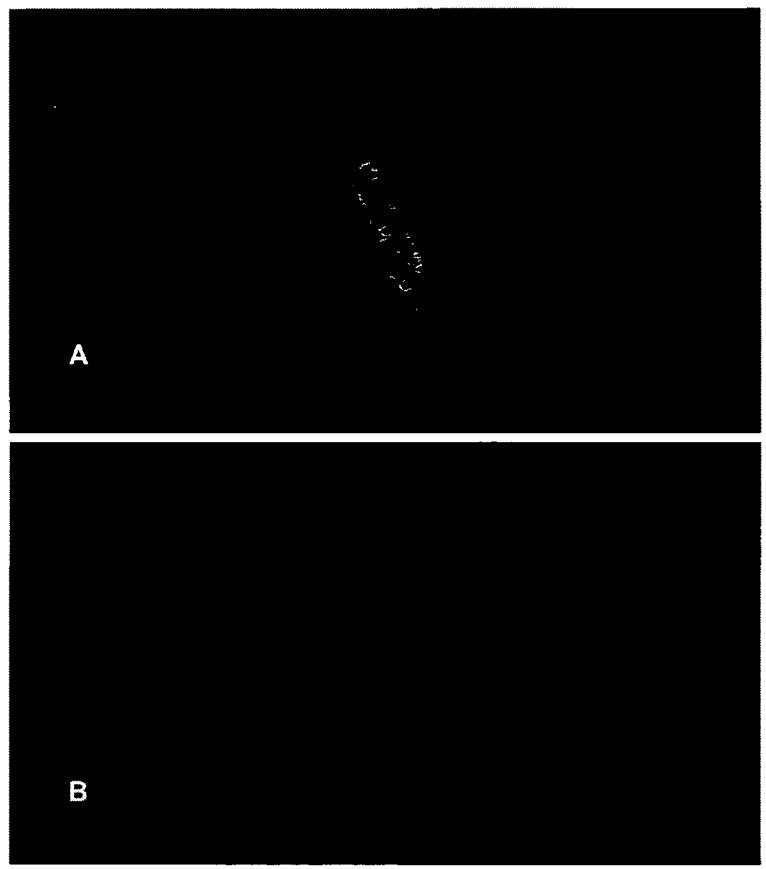
FIGS. 6A and 6B are photomicrographs showing vesicles of the presently disclosed subject matter used to deliver biotinylated lipids to a femoral vein. Rat hindlimbs were perfused with vesicles containing biotinylated PE.

Examples of lipid soluble biomolecules that can be delivered by a vesicle disclosed herein comprising lipid soluble biomolecules includes, but is not limited to α-tocopherol (vitamin E), retinol (vitamin A), phyllochinon (vitamin K), ergocalciferol (vitamin D), cholesterol, cholesterol esters, steroids, hopanoids, detergents, fatty acids, branched fatty acids (such as found in bacteria), isoprenoids, long chain alcohols, and anesthetics, gangliosides, lipopolysaccharides, biotin-labeled phospholipids, membrane bound proteins, membrane ion conductance channels (e.g., Na/K-ATPase, H-ATPase, Ca-channels, Na-channels, K-channels, Cl-channels), transport proteins, glucose transporters, GLUT-1, GLUT-2, GLUT-3, GLUT-4), adhesion proteins, gap junction proteins, synaptic junction proteins, caspases, adherence proteins (e.g., ICAM, PECAM, VCAM), G-proteins, Major Histocompatibility Complex (MHC) proteins, complement proteins, viral proteins, cellular receptors, lipid-soluble fluorescent probes, and lipid-soluble radioactive tracers. For example, FIGS. 6A and 6B depict a section of rat femoral vein stained with a membrane bound fluorescent probe delivered using lipid vesicles disclosed herein.

Water-soluble molecules can also be delivered to target cells by encapsulation of the biomolecules within the aqueous compartment of the vesicles disclosed herein. A wide variety of water-soluble molecules can be delivered by the lipid vesicles of the presently disclosed subject matter with few limiting criteria, such as that the molecules can fit within the interior of the lipid vesicle. At an average size of 200 nm, most biomolecules would fit into this space. Examples of water-soluble biomolecules that can be encapsulated within the lipid vesicles of the presently disclosed subject matter include, but are not limited to amino acids, peptides, polypeptides, proteins, monosaccharides, disaccharides, polysaccharides, nucleotides and polynucleotides (e.g., DNA, RNA, mRNA, tRNA, sRNA, and miRNA), water soluble vitamins, minerals, high energy phosphates (e.g., adenosine triphosphate (ATP), adenosine diphosphate (ADP), adenosine monophosphate (AMP), adenosine, cytosine triphosphate (CTP), cytosine diphosphate (CDP), cytosine monophosphate (CMP), cytosine, uracil triphosphate (UTP), uracil diphosphate (UDP), uracil monophosphate (UMP), uracil, guanosine triphosphate (GTP), guanosine diphosphate (GDP), guanosine monophosphate (GMP), guanosine, thymine triphosphate (TTP), thymine diphosphate (TDP), thymine monophosphate (TMP), thymine, inosine triphosphate (ITP), inosine diphosphate (IDP), inosine monophosphate (IMP), and inosine), phosphocreatine, glycolytic intermediates (e.g., glucose, glucose-6-phosphate, glucose-1,6-bisphosphate, FDP, DHA-P, G-3-P, PEP, and pyruvate), oxidative intermediates (e.g., acetyl Co-A, citrate, and isocitrate), nicotinadenine dinucleotide (NADH), flavin adenine dinucleotide (FADH2), water-soluble cellular enzymes, insulin, water-soluble fluorescent probes, water-soluble radioactive tracers, and water-soluble drugs.

In some embodiments of the presently disclosed subject matter, ATP is a biomolecule incorporated into the lipid vesicle. There are several different salts of adenosine-5'-triphosphate (ATP) that can be utilized with the presently disclosed subject matter, including magnesium ATP (Mg-ATP), disodium salt of ATP, dipotassium salt of ATP, and di-Tris salt of ATP.

The Mg-salt (Mg II) of ATP is utilized for a representative embodiment. The Mg-salt of ATP has a slightly greater $\Delta G'$ of hydrolysis of the gamma phosphate, and more than 90% of all cellular ATP is found as the magnesium salt. Although the $\Delta G'$ of hydrolysis of Mg-ATP has been reported as $-8.4$ kcal/mol, it can differ within the cytosol of the cell. For example, the $\Delta G'$ of hydrolysis for Mg-ATP can be affected by pH and other divalent metals present. In certain circumstances, the $\Delta G'$ of hydrolysis for Mg-ATP could be as high as $-12.5$ kcal/mol within a cell.

An important feature of Mg-ATP is its central role as the ultimate source of high energy phosphate as either a donor (e.g., glucose-6-phosphate) or an acceptor (e.g., creatine phosphate). Mg-ATP acts as a central regulator of all high energy phosphates by its negative feedback roles in the cell. For example, as intracellular Mg-ATP levels increase there is an inhibition of phosphofructokinase, decreasing the utilization of glucose. In addition, to its central intracellular role, Mg-ATP also plays an extracellular role in several different ways. For example, Mg-ATP binds to and activates purinergic receptors ($P_2X$), leading to a variety of intracellular affects, including but not limited to, depolarization by $K^+$ entry, increased intracellular calcium, activation of protein kinases, cellular retraction, nitric oxide (NO) release, and vascular smooth muscle cell (VSMC) relaxation. Recent advances in the synthetic manufacturing of ATP through either bioreaction or synthesis have significantly improved the quality and quantity of Mg-ATP available in the commercial market.

The magnesium or other salt of ATP can be incorporated into the vesicle in some embodiments, and can be added at the time of lipid re-hydration. ATP concentration can vary and will depend on the specific application. Concentrations of ATP used in some embodiments include about 0.001 mM to about 1 M, and in some embodiments, about 1 mM to about 200 mM or about 1 mM to about 50 mM. In particular embodiments the concentration of ATP can be about 0.1 mM, 1 mM, 2.5 mM, 5 mM, 7.5 mM, 10 mM, 25 mM, or 50 mM. The buffer containing the ATP can have a low protein content to decrease the chance of non-specific absorption of the lipid material. SUVs that contain ATP are referred to as ATP-SUV for convenience.

Encapsulation of ATP by SUVs can be assessed. For example, labeled ATP molecules (such that the label does not interfere with vesicle formation), such as radiolabeled ATP is used. Radiolabels include $^{32}P$ and $^3H$, and are added when the lipids are re-hydrated after drying, prior to agitation. The solution is applied to a Sephadex G-25 column (or other suitable matrix) to remove non-encapsulated ATP. The effluent from the column is collected and assayed for the presence of vesicles. SUVs are usually eluted in the earliest fractions. Percent encapsulation is determined by quantifying the radioactivity in the vesicle and supernatant fractions, and determining the proportion of encapsulated ATP and multiplying by 100. Preferable encapsulation percentages range from approximately 1% to 20%.

Molecules other than ATP may be delivered to cells using SUVs, such as organic and inorganic molecules, including pharmaceuticals, polypeptides, nucleic acids and antibodies that interact with intracellular antigens.

Assays for Measuring SUV Absorptivity

The absorption rate can be quantified as a measure of the number of lipid vesicles that absorb (e.g., fuse) with HUVEC cells in a well/second (about $10^6$ cells). The assay comprises the following steps:

(1) HUVEC cells (American Type Culture Collection (ATCC); Manassas, Va. or BioWhittaker; Maryland) are cultured;

(2) SUVs are prepared and loaded with a fluorescent probe, such as carboxyfluorescein;

(3) the SUVs are contacted to the cells to allow for absorption;

(4) at a selected time, any residual SUVs are removed; and (5) fluorescence is measured.

The presence and intensity of a fluorescent signal after removing the SUVs indicates the ability of the SUVs to absorb with the cell membranes and deliver the contents.

Human umbilical vein endothelial cells (HUVECs) is given as an example. The cells are grown to confluence on a standard 12-well culture dish (for example, from COSTAR; the number of cells is approximately $10^6$) in endothelial cell growth medium (EGM). The HUVECs are then washed 3 times with a buffer, such as HBSS. Prepared lipid vesicles (such as for example, DOPC/DOPC-e (1:1); DOPC/POPA (50:1), DOPC/POPA (1:1), PS, PG, MPC, PE, cit-DOPC and cit-DOPCe), are loaded with 1 mM carboxyfluorescein. The vesicles are incubated with the cells for 120 minutes, assaying fluorescence at each 5 minute increment, at 37° C., 95% air/5% $CO_2$, after which time residual vesicles are removed by washing the cells with buffer. If negatively charged lipid vesicles are used, calcium (final concentration 0.1-10 mM) is added at the absorption step.

Cells are removed from the dish by treating with trypsin. Fluorescence is measured (excitation at 495 nm and emission of 520 nm) using a fluorescence spectrophotometer or other suitable device.

In some embodiments, the rate of absorption for biomolecule-SUV compositions is approximately 20 vesicle absorptions/second/cell to $8.0 \times 10^{11}$ vesicle absorptions/second/cell, including 500 to $1 \times 10^8$ vesicle absorptions; 750,000 to $50 \times 10^7$ vesicle absorptions/second/cell; $5 \times 10^6$ to $1 \times 10^7$ vesicle absorptions/second/cell; including $1 \times 10^6$ to $8 \times 10^8$ vesicle absorptions/second/cell; $1 \times 10^7$ to $5 \times 10^8$ vesicle absorptions/second; and $5 \times 10^7$ to $1 \times 10^8$ vesicle absorptions/second/cell. Examples of absorption rates are at least 100, 1000, $10^4$, $10^5$, $10^6$, $10^7$, $10^8$, $10^9$, $10^{10}$, and $10^{11}$ vesicle absorptions/second/cell. Some of these values were obtained experimentally at 37° C. using mixtures of DOPC and DOPC/DOPC-e and DOPC/POPA, with and without calcium, and using human endothelial cells. The absorptive rate of the lipid vesicles can vary from cell to cell. In addition, the absorptive rate can be affected by temperature, ionic strength, and pressure.

Because the lipid composition of plasma membranes varies by cell type, the choice of cells for use in the assay is carefully considered, and should match as best the target cell type(s). For example, liver cell plasma membranes consist of about 7% phosphatidylethanolamine, while red blood cell plasma membranes contain 18% (Alberts et al. 2002). Primary culture cells, as well as cell lines (available from the American Type Tissue Collection (ATCC); Manassas, Va.) are useful, although primary cultures are preferred because of the likelihood that the plasma membrane lipid composition is altered in transformed cells. Cell types include pancreas, intestinal, immune system, neuronal (including those of the brain, eye, nose and ear), lung, heart, blood, circulatory (lymph and blood), bone, cartilage, reproductive, glandular, enamel, adipose, skin, and hepatic. Cell lines include those derived from these tissues, such as Madin-Darby canine kidney (MDCK), Chinese hamster ovary (CHO), HeLa, etc. Cells may be from other organisms, such as plants, fungi (including yeasts), and bacteria. Examples of absorption rates with these other cell types include at least 100, 1000, $10^4$, $10^5$, $10^6$, $10^7$, $10^8$, $10^9$, $10^{10}$, and $10^{11}$ vesicle absorptions/second/cell. Unless otherwise specified, absorption rates are with respect to HUVECs under the conditions specified above. Absorption rates with respects to other cell types is for about $10^6$ cell, with a buffer, such as HBSS, and the vesicles are incubated with the cells for 120 minutes at 37° C., 95% air/5% $CO_2$, after which time residual vesicles are removed by washing the cells with buffer.

Assays for Optimizing Absorption Rates

The assay for absorption rate can be further modified when optimizing the absorption rate of a particular vesicle composition with a particular cell type. For example, the lipid vesicle can contain a fluorescent or radioactive tracer that is part of the membrane bilayer of the vesicle.

Fluorescent probes that can be utilized include, but are not limited to fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; and 4,4-difluoro-4-bora-3a,4a-diaza-s-indacene. The excitation wavelength will vary for these compounds. Lipid vesicles are made in the presence of the tracer in ratios such as 1:800 lipid/probe. Other useful ratios include 1:200 to 1:10,000, including 1:400, 1:500, 1:600, 1:700, 1:800, 1:900 and 1:1000.

Altering Absorption Rates

The absorption rate of any lipid vesicle can be altered by changing a variety of factors, such as temperature, ions, lipid concentration, lipid vesicle composition, flow rates, lipid vesicle size, etc. Altering the phospholipid formulation of lipid vesicles can be used to maximize absorption rates as well as minimize toxicity. For example, to preserve organs for transplant or cells in suspension (such as blood), lipid vesicles that have slower, delayed absorption rates are desirable. Such rates can be obtained with vesicles comprising only DOPC. On the other hand, if immediate raising of the intracellular concentration of a biomolecule is crucial, as for example in stroke, heart attack or trauma sufferers, lipid vesicles with very fast rates of delivery are desirable. DOPC/POPA compositions, for example, deliver biomolecules such as ATP for example at sufficient concentrations to meet metabolic demand of affected tissues in less than five minutes (see Examples).

Four general approaches can be used to alter absorption rates by manipulating lipid composition:
(1) increasing electrostatic interactions;
(2) destabilizing membrane bilayers;
(3) increasing non-bilayer phases; and
(4) creating dissimilar lipid phases.

Increasing Electrostatic Interactions

Electrostatic interactions can be exploited to increase absorption rates. Phospholipids are classified according to their charge (cationic, anionic, and zwitterionic). Many of the cationic phospholipids, such as PE, and anionic phospholipids, such as phosphatidic acid (POPA), do not form closed vesicles at physiologic pH. However, anionic and cationic lipids mixed with zwitterionic phosphatidylcholines can form closed vesicles at physiologic pH.

The plasma membrane of most cells has a net negative charge. Because of this negative charge, there is a layer of counterbalancing ions, typically calcium, magnesium, sodium and potassium, which presents a net positive charge. Taking advantage of the electrostatic interaction between liposomes and plasma membranes, lipid vesicles can be engineered to have a net negative charge, thus maximizing cell-lipid vesicle absorption. However, some cell plasma membranes contain more cationic lipids, which are counterbalanced by an anionic ion layer. In these situations, lipid vesicles are engineered to have a net positive charge to maximize cell-lipid absorption.

Creating Dissimilar Lipid Phases

Plasma membranes contain lipid domains or rafts that are enriched in a particular lipid species. At the boundary of such a membrane raft are regions of dissimilar lipid species. These regions have the potential for instability, effecting how the membrane interacts with other membranes. Several phospholipids are known to increase lipid raft formation, including mixtures of phosphatidylcholines, sphingomyelin, and cholesterol. For example, DOPC, 18:0 sphingomyelin, and cholesterol are mixed in a 1:1:1 ratio during lipid vesicle preparation. Cholesterol preferentially partitions in the sphingomyelin phase, creating regions that are rich in DOPC and poor in cholesterol, and regions that are rich in sphingomyelin and rich in cholesterol.

Changing the physical parameters of absorption, temperature, concentration, ionic strength, and absorption period, can be used to affect absorption rates. By altering temperature, the free energy (G) of the system is altered, leading to different rates of absorption. Increasing lipid vesicle concentration also affects membrane absorption rates, especially at very high concentrations. The absorption period (length of absorption) and the number of absorption periods also affect the rate of delivery of the encapsulated contents of SUVs.

Temperature

Lipid vesicles containing ATP, for example, are incubated with tissues 5, 10, 15, 30, 60 or 120 minutes at the temperatures at which the tissues are being preserved (4° C.—hypothermia, 22° C.—room temperature, 37° C.—normothermia). Increasing the temperature of the vesicle solution leads to increased kinetic energy of the vesicles and hence increased capability to absorb. Temperature also affects the free diffusion of the vesicles.

Concentration on Vesicle Absorption

While intuitive that increased concentration leads to increased lipid vesicle content delivery, the rate of membrane fusion is not linear. Once lipid vesicle lipids occupy all of the available plasma membrane surface, further absorption is limited. The extent of absorption with the plasma membrane affects membrane volume and properties, such as ion permeability and lipid organization. Therefore, when administering SUVs, SUV concentration must be controlled so that the target cells are effectively treated.

Absorption Period

The length of time that absorption is allowed to occur helps to control the extent to which encapsulated substances are delivered. Preferable absorption periods include 1-180 minutes, such as 1, 5, 10, 30, 60, 120 and 180 minutes. To halt absorption, the vesicles are removed (such as by washing with a buffer), or the concentration of the administered vesicles is such that the vesicles are depleted at the end point of the desired time. Absorption may also be optimized such that the total delivery of the vesicles is controlled through one or multiple administrations. For example, if the target absorption period is 120 minutes, two 60 minute periods may be used, or four 30 minute, twelve 10 minute, or 24 five minute absorption periods. Provided that proper equipment is available, 1 minute or less absorption periods may also be accomplished, although these periods are often inconvenient and technically demanding.

Determining Biomolecule Requirements of the Targeted Cells and Tissues

The optimum rate of biomolecule administration is that which approximates the basal demand of the cells for the particular biomolecule, such as for example the basal metabolic ATP demand of cells, which can be determined by any method known in the art. For example, oxygen consumption rates, pyruvate, glucose, lactate, and proton leak can be calculated, and from this data, the ATP consumption of the tissues is determined as ATP consumed/minute.

Measuring Rates of ATP Hydrolysis

Intracellular ATP levels can be measured using one of several techniques generally known in the art. For example, HPLC provides information of the nucleotide contents of the cell, but is limited in that it provides a "snap-shot" of the nucleotide levels at a given time. $^{31}$P-NMR can be a more preferred method of measuring intracellular nucleotides in certain circumstances as it provides a dynamic measure of the ATP levels in the cell.

Membrane Potential and Proton Leak

Tissue samples are isolated and incubated with the membrane potential fluorescent probe MC540 (Sigma; St. Louis, Mo.). Changes in fluorescence of MC540 upon addition of various amounts of potassium are measured as an indice of membrane potential and proton leak as previously described (Brand, 1995).

Glucose, Pyruvate, and Lactate Levels

These metabolic intermediates are determined using standard methods or commercially-available analysis kits (such as those available from Sigma). The levels of these intermediates are adjusted to protein levels and are measured over a 120 minute time period.

Determination of ATP Consumption

From the rates of lactate, pyruvate, and glucose accumulation, oxygen consumption, and proton leak, it is possible to calculate all of the fluxes through the system by using reaction stoichiometries as described by Ainscow and Brand (1999).

Administration

Pharmaceutical Compositions

In many cases, the presently disclosed vesicles may be delivered as a simple composition comprising the vesicles, which may also comprise a biomolecule, and the buffer with which it was made. However, other products may be added, if desired, such as those traditionally used as carriers in pharmaceutical compositions.

A "pharmaceutically acceptable carrier" includes any and all solvents, dispersion media, coatings, antibacterial and antifungal agents, isotonic and absorption delaying agents, and the like, compatible with pharmaceutical administration (Remington 2000). Preferred examples of such carriers or diluents include water, saline, Ringer's solutions and dextrose solution. Supplementary active compounds can also be incorporated into the compositions.

General Administration Considerations

A pharmaceutical composition of the presently disclosed subject matter is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

If negatively charged lipid vesicles are used in the compositions disclosed herein, calcium can be included such that the final concentration at the site of absorption is preferably 0.1 mM-10 mM; including 0.1, 1, 2, 3, 4, 5, 6, 7, 8, 9 or 10 mM.

In ATP-lipid vesicles, for example, the ATP is usually in equilibrium with the ATP in any solution surrounding the ATP-SUVs; typically only 1-10% of the total ATP is within the ATP-SUVs. The remaining ATP may bind to receptors, such as the purinoreceptor P2y, causing ions to flow out of the cells, and interfering with ion balance and homeostasis. Although the cells can usually reestablish ion balance and homeostasis, this consumes additional ATP. Therefore, particularly with tissue for which immediate restoration of function is desirable (for example, during organ transplantation, or limb reattachment), including in the composition one or more purinoreceptor P2y antagonists, can be advantageous. The purinoreceptor P2y antagonists can be added to the composition after forming the vesicles, or just prior to administration, since the antagonists do not need to be within the SUVs. Examples of purinoreceptor P2y antagonists include pyridoxal 5-phoshpate, vitamin B6 (pyridoxal-5-phosphoric acid), and Reactive Blue 2 (1-amino-4-[[4-[[4-chloro-6-[[3 (or 4)-sulfophenyl]amino]-1,3,5-triazin-2-yl]amino]-3-sulfophenyl]amino-9,10-dihydro-9,10-dioxo-2-anthracenesulfonic acid), and combinations thereof. The purinoreceptor P2y antagonists may preferably be used in a concentration of 0.1 to 250 micromoles/L, more preferably 1-100 micromoles/L.

Injectable Formulations

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as mannitol, sorbitol, and sodium chloride can be included in the composition. Compositions that can delay absorption include agents such as aluminum monostearate and gelatin.

Sterile injectable solutions can be prepared by incorporating lipid vesicles disclosed herein in the required amount in an appropriate solvent with one or a combination of ingredients as required, followed by sterilization. Methods of preparation of sterile solids for the preparation of sterile injectable solutions include vacuum drying and freeze-drying to yield a solid containing lipid vesicles and any desired ingredient (such as a biomolecule, e.g., ATP) in sterile solutions.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Transmucosal or Transdermal

Administration can be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams. Suppositories (e.g., with bases such as cocoa butter and other glycerides) or retention enemas for rectal delivery may also be prepared.

Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Dosage

Dosage is dictated by, and directly depends on, the unique characteristics of the lipid vesicle, which varies with different lipid compositions, the particular desired therapeutic effect, and the route of administration. The specific dose level and frequency for any particular patient or application may be varied. Factors that should be considered, including (1) the temperature at which administration is made and at which absorption is permitted; (2) the ionic environment of the administration site and the ionic strength of the lipid vesicle composition; and (3) the length of time that absorption is permitted. Controlling these factors helps to control the extent to which the encapsulated substances, including for example ATP, are delivered.

When administering lipid vesicles, lipid vesicle concentration is controlled to effectively treat the target cells while not inhibiting their function by saturating the plasma membranes with lipid vesicles lipids. Preferable concentrations of lipid vesicles, depending on lipid composition, target cell dispersion and volume to be administered may be 0.5 mg/ml-100 mg/ml, such as 0.5 mg/ml, 1 mg/ml, 5 mg/ml, 10 mg/ml, 20 mg/ml, 30 mg/ml, 40 mg/ml, 50 mg/ml, 60 mg/ml, 70 mg/ml, 80 mg/ml, 90 mg/ml and 100 mg/ml.

Vesicle absorption occurring via electrostatic interactions is significantly affected by changes in calcium and/or magnesium concentrations, and to a lesser extent, changes in sodium and/or potassium concentrations. Modulating these ion concentrations either in the compositions used to administer the lipid vesicles or in compositions administered to a target site before or after vesicle administration, affect dosage considerations. Preferably, ion concentrations of 0.01 nM to 1 mM, including 0.1 nM, 1 nM, 10 nM, 100 nM, 1000 nM, 10 micromole/L, and 100 micromoles/L are used. Combinations of these and other ions may also be used.

Regimes of chronic administration or single dosing can be used and are chosen according to the type of treatment, administration route, and the vesicles themselves. Preferable absorption periods include 1-180 minutes, such as 1, 5, 10, 30, 60, 120 and 180 minutes. To halt absorption, the vesicle is removed (such as by washing with a buffer), or the concentration of vesicles is such that the vesicles are depleted at the end point of the desired time. Absorption can also be optimized such that the total delivery of the vesicles is controlled through one or multiple administrations. For example, if the absorption period is 120 minutes, two 60 minute periods may be used, or four 30 minute periods, twelve 10 minute periods, or 24 five minute absorption periods.

Uses for ATP-SUV

Because of the universal cellular requirement for ATP, ATP-SUV and other SUV/ATP compositions have a broad array of applications that span the biological kingdoms.

It has been determined that simple lipid vesicles generally, when injected intravenously (IV), have very short circulating times (on the order of 15 min-2 hr) (Oku et al. 1994). For pharmaceutical drug use, this is not highly advantageous for maximal tissue distribution as the drug is rapidly cleared by the reticuloendothelial system (RES). Substances that can potentially "mask" the lipid vesicle, such as polyethylene glycol, gangliosides, sulfatides as part of the lipid vesicle, can create "stealth vesicles" (Oku et al. 1994). Stealth vesicles allow for much longer circulating times (in excess of 24 hrs up to 2-3 days). For an antibiotic or a drug that requires slow release, this can be advantageous. However, during periods of ischemia when rapid delivery of ATP to tissue is needed, this type of lipid vesicle is the exact opposite of what is desired in terms of its delivery characteristics. For example, in the heart, the maximal tolerable ischemic time is about 10 minutes (Childs & Lower 1969), and a lipid vesicle that is "stealthy" would not sufficiently increase heart ATP levels rapidly, as needed.

The interaction of ATP-SUV with the RES system has been documented in vivo. ATP-SUV when given IV can interact very rapidly with endothelial cells and macrophages.

Research by the inventors over the last 10 years has demonstrated that the vascular endothelium is one of the major culprits in ischemia-reperfusion injury. Thus, there it can be beneficial to maintain endothelial cell ATP levels during severe ischemia (Ehringer et al. 2000, Ehringer et al. 2006 (In press), Ehringer et al. 2001, Ehringer et al. 2002). Decreased endothelial cell ATP levels can lead to the accumulation of hypoxanthine, which upon reperfusion is converted into xanthine and oxygen radicals (Albrecht et al. 2003). In addition, the endothelium is also much more sensitive to low-flow ischemic conditions (Eltzschig & Collard 2004), which ultimately can lead to acidosis and the accumulation of metabolic waste by-products (e.g., flushing tissue with saline can decrease reperfusion injury). Studies by the inventors on endothelial cells, blood vessels, composite tissues, organs, and organisms all suggest that the endothelium can be a significant area of uptake of ATP-SUV. A percentage of ATP-SUV also escapes into the parenchymal space and may be taken-up by cells outside of the vasculature. A good example appears to be the heart, where the inventors have detected a near doubling of myocardial ATP under hypoxia in the presence of ATP-SUV (compared to lactated ringers only).

The RES also is composed of the immune cells, especially monocytes, which through phagocytosis, leads to the accumulation of ATP-SUV in these cells and in the endothelium. The most active of these cells of the RES are the Kupfer cells of the liver (Arii & Imamura 2000), a very important cell that is highly susceptible to hypoxia. Kupfer cells, neutrophils, lymphocytes, and even RBCs, are actively taking up ATP-SUV vesicles (either through fusion or phagocytosis) by a variety of mechanisms. This maintains ATP levels in these oxidant-sensitive cells, and leads to less reperfusion by-products.

ATP-SUV is selectively targeted for maximum uptake by the RES for several reasons. First, ATP-SUV comprises a fluid bilayer, composed in some embodiments of mainly phosphatidylcholine to which is added an unstable vesicle forming member, or "fusogen". Pusieux et al. (1994) have used vesicles containing PC, cholesterol, and sulfatide, the main constituents of a stealth liposome and not possessing the rapid delivery characteristics of the ATP-SUV disclosed herein. Arkawa et al. (1998) use PC and cholesterol at various ratios to achieve higher plasma levels of ATP with very slow ATP delivery to tissues. In fact, this same group reported that, "about 35% of encapsulated ATP was released from the liposomes after 90 hours at 37° C." Arkawa et al. 1998. In either case, the amount of ATP delivered to cells that are most sensitive to ischemia, the endothelial cells and the WBC, are minimal. At physiological temperature, the fluid nature of the vesicles accelerates the clearance of the ATP-SUV from the blood stream to the RES. In addition, ATP-SUV can carry a net charge, which is freely accessible to the cells of the RES. This charge density increases ATP-SUV clearance and absorption into the RES. In addition, the size of the vesicles, in the order of 100-200 nm in some embodiments, makes the vesicles more likely to be taken up by the cells of the RES.

Blood

Blood can be stored under refrigeration for about 45 days before the red blood cells become nonviable. Red blood cells typically survive in circulation for about 120 days, after which the spleen and liver remove and destroy them. Thus if nonviable cells are transfused, they likewise are removed immediately from circulation.

The addition of ATP-SUV or other SUV-encapsulated ATP compositions to collected blood sustains the red blood cells longer, increasing viable storage time and the likelihood that the cells will remain in circulation and not destroyed.

The lipid compositions may be altered to optimize ATP delivery. For example, because blood is stored at 4° C., metabolic demand for ATP will be low. Even though the absorption rate of SUVs will also be slowed at this temperature, the rate may be too high for viable storage and SUV lipid compositions are derived to better match the metabolic demands of the blood cells.

When whole collected blood is stored in contact with the compositions of the presently disclosed subject matter, the white blood cells and platelets will also benefit and remain viable longer.

Sustaining Amputated Body Parts for Replantation

After the (usually inadvertent) amputation of a body part, the success of replantation depends in large part on the ability of the appendage to survive apart from its owner. The longer the ischemic time, the less likelihood that replantation results in a functional appendage, or even success of any kind at all.

In one example, the major feed artery of a recovered severed limb is cannulated for perfusion. The limb is perfused with the ATP-SUV every 4 hours, or as determined necessary due to changes in tissue ATP levels. The arterial pressure of the limb is monitored during perfusion to decrease the chance of flow-induced injury, and to monitor the overall preservation of the severed limb—higher perfusion pressures may indicate limb morbidity. Following the preservation period, the limb is flushed with Ringers or other suitable solution to remove traces of ATP-SUV. The limb is then surgically reattached using well-known methods. External indices of limb function after anastomoses are evaluated (color, evidence of microthrombi, temperature, pulse, oxygen saturation, Doppler flow measurements) to monitor success. Prior to and following replantation, heparin is applied and antibiotic therapy is commenced to reduce the likelihood of infection.

Heart Arrest

The ATP-SUV is injected into the heart by intravenous or intracardiac injection, immediately or as soon as possible following the hypoxic episode. The SUV lipid compositions are manipulated so that ATP delivery is carefully matched to the metabolic demand of heart tissue, maximizing heart performance. ATP-SUV may be constantly perfused into the heart at physiologic conditions until such time the danger of ischemia has passed.

Delivering ATP for Organ Preservation

Organs (e.g., hearts, liver, lungs, kidney or pancreas) are removed from the donor, and the major feed artery into the organ is cannulated. The blood in the organ is flushed from the organ using saline, Ringers solution or other suitable solution. ATP-SUV is added to regular preservation solutions or to buffer, and gently perfused (≥80 mm Hg) into the organ, the frequency of which will depend on the organ.

The same ATP-SUV can be used in the animal laboratory setting. For example, a Lagendorff heart (or other organ) perfusion apparatus is used. The aorta is cannulated and the heart is placed into a perfusion chamber. The heart is perfused with an oxygenated perfusate to which ATP-SUV has been added. A high concentration potassium solution may be injected to cause cardiac arrest. A cardioplegia with ATP-SUV can be used during the preservation period. The heart can be reperfused for functional studies or can be transplanted after ischemic preservation.

Delivering ATP Systemically

ATP-SUV can be administered to organisms for a variety of reasons. For example, ATP-SUV can be used to supplement energy in the body (preferred administration routes are oral, topical and inhaled), or it can be used to decrease the reliance upon oxygen for the whole body (preferred administration route in this case would be intravenously). When ATP-SUV is administered to animals by continuous infusion via the carotid artery, heart rates and blood pressure decrease and respiration ceases. The animals can be resuscitated, even after 9 minutes of hypoxia (see Examples).

ATP-SUV for Wounds

Because blood flow to wounds is diminished, less oxygen is available to the cells in and around the wound. The decrease in oxygen delivery results in a decrease in ATP production, which slows many cellular events necessary for wound healing, including protein and nucleic acid synthesis, ion channel function, signal transduction, and locomotion.

ATP-SUV is applied to the wound as necessitated by the extent of healing or the ATP consumption of the wound. For example, to provide the border cells of the wound sufficient ATP to accelerate wound closure, ATP-SUV may be applied preferably 1-12 times per day, such as 1, 2, 3, 4, 5, 6, 7, 8, 9, 10, 11 or 12 times/day. Preferably, the ATP-SUV is placed directly over the wound in a specially designed applicator which keeps the water-based ATP-SUV in direct contact with the wound border cells. Alternatively, the ATP-SUV may be applied topically as a cream or other topical pharmaceutical composition.

ATP-SUV may also be combined with healing compositions already available to further enhance healing. For example, ATP-SUV can be combined in a composition with becaplermin, as found in REGRANEX® (Ethicon, Johnson & Johnson, Somerville, N.J.). In addition, the ATP-SUV can be co-applied with or combined in a composition with growth factors (e.g. fibroblast growth factor and vascular endothelial growth factor), one or more antibiotics, silver containing wound ointments, and/or topical oxygen therapy. Additional wound-treating components useful with the ATP-SUV include antiseptics, antibiotics, anesthetics, and skin graft compositions. The term "wound-treating component" does not include SUVs.

"Skin graft composition", as the term is used herein, refers to natural and manufactured materials useful for the temporary or permanent replacement of skin tissue, due to for example damage, such as from burns, other skin trauma, or even aging. "Natural" materials would include epidermal and/or dermal tissue derived from donor tissue. The donor tissue can be derived from the patient receiving the skin graft composition (i.e., autologous tissue), from a different individual of the same species (i.e., allogeneic tissue), or from a donor organism of a different species from the recipient (i.e., xenogeneic tissue). The donor tissue can be treated prior to transplant to, for example, decrease the risk of immune rejection by the recipient, or to enrich or deplete certain components of the tissue, such as for example certain cells including but not limited to dermal cells (e.g., fibroblasts) and epidermal cells (e.g., keratinocytes). "Manufactured materials" as used herein includes entirely synthetic skin substitutes (such as for example collagen-based matrices) as well as hybrid compositions comprising both living tissue (such as for example fibroblasts and/or keratinocytes) and synthetic biomaterials (such as for example biodegradable scaffolding). In particular, manufactured skin graft compositions include for example "artificial skin" compositions including TRANSCYTE® (Smith & Nephew, San Diego, Calif.), which comprises a human fibroblast derived skin substitute and INTEGRA® (Integra Life LifeSciences, Plainsboro, N.J.), which comprises a bilayer membrane system for replacement of dermal tissue. See for example, U.S. Pat. No. 4,947,840, herein incorporated by reference, which discloses the composition of and uses for the INTEGRA® skin replacement composition. The ATP-SUV disclosed herein can be co-applied along with the skin graft composition(s) to facilitate wound healing.

ATP-SUV for Hemmorhagic Shock

Hemmorhagic shock results from losing large amounts of blood, caused by internal or external injuries. Because the blood supply is insufficient, the subject often becomes hypotensive, resulting in organ failure and imminent death.

To counter the effects of hemmorhagic shock, ATP-SUV is infused intravenously as a supplement to blood transfusion. The ATP-SUV can then be decreased as whole body oxygenation improves. See Example 9 for data showing the effectiveness of ATP-SUV for countering the effects of hemorrhagic shock.

ATP-SUV for Platelet Storage

Platelets have a shelf-life of about 5 days, after which they must be discarded. The loss of platelet function is partly due to loss of ATP.

Isolated platelets are given ATP-SUV as needed to maintain intracellular ATP levels. The shelf life of the platelets is then extended. ATP-SUV is suspended in a suitable solution for platelet storage, such as saline. The SUV lipid compositions may be altered to optimize ATP administration. For example, because platelets are stored at room temperature (22-24° C.), metabolic demand for ATP will be lower than at physiologic temperature (37° C.). Even though the fusion rate of SUVs will also be slowed at this temperature, the rate may be too high for viable storage and SUV lipid compositions are derived to better match the metabolic demands of the platelets.

ATP-SUV for Organ and Tissue Engineering

Tissues can now be grown in vitro with great efficiency. However, such tissues lack a vasculature to connect to the blood supply. ATP-SUV helps overcome this defect.

ATP-SUV can be used to selectively preserve a blood vessel network derived from isolated tissue, such as a skeletal muscle. The lipid composition of the ATP-SUV is made such that the ATP-SUV does not easily escape from the blood vessels. Administration of ATP-SUV maintains the vasculature, but not the parenchyma, which dies. The intact vasculature is then be seeded and cultured under appropriate conditions with stem cells that are competent to differentiate into specific tissues. In vitro-produced tissues that can be vascularized in this manner include liver, pancreas, heart, lung and spleen.

Alternatively, organs already undergoing in vitro construction can be partially vascularized using this same approach, except the vasculature is harvested and treated after the organ cells have started growing.

ATP-SUV During Surgery

Decreased blood flow and oxygen are inflicted during major surgical procedures. ATP-SUV can be administered to the whole body or to the areas which are involved in surgical procedures to minimize any damage from ischemia or hypoxia. Examples of surgeries in which ATP-SUV is useful include coronary bypass, open-heart surgery, free flap transfer, and some plastic surgery procedures.

In some surgeries, paralysis sometimes results because the spinal cord does not receive sufficient oxygen during the procedure. This occurs mainly in aortic aneurysm resection. The application of ATP-SUV to the affected areas or administered intravenously allows surgeons more time to work, and decreases the likelihood of loss-of-oxygen-induced injuries, and results in decreased morbidity.

ATP-SUV for Stroke

Currently, administration of a high glucose solution immediately following a stroke is used to decrease the effects of decreased blood flow to the brain. The glucose is expected to increase neural cell ATP levels and decreases neural cell death. However, this goal is difficult to achieve when oxygen supply is limited. ATP-SUV would provide neural tissues with ATP more efficiently.

ATP-SUV for Respiratory Problems

Many respiratory aliments decrease the quality of life, and often lead to death. In these cases, the major leading cause of death is a lack of oxygen in the blood, resulting in tissue and organ death. Subjects are infused with ATP-SUV to decrease the effects of decreased blood oxygen levels.

ATP-SUV for Cancer Patients

End-stage cancer patients die from resulting complications. Because cancer or therapies have weakened them, cancer patients often die from pneumonia. The weakness results from either the cancer cells usurping valuable metabolic resources and thus impoverishing healthy cells, or non-cancer healthy cells being destroyed during therapy, or both. Cancer patients are administered ATP-SUV daily to supplement whole body ATP levels and thus decrease the effects of the cancer cells appropriating metabolic resources. By administering ATP-SUV, sequellae from cancer are decreased, and life expectancy is extended.

ATP-SUV for Chemical Poisons

Cyanide and other chemicals that block mitochondrial ATP production or otherwise decrease cellular ATP production can be thwarted by using ATP-SUV. ATP-SUV maintains cell and tissue viability and function when bathed in cyanide—ATP-SUV increases cytosolic ATP in the absence of mitochondrial ATP production. ATP-SUV can be used as an antidote for cyanide and for other poisons that act in a similar manner as cyanide. See Example 10 for experimental data showing the effectiveness of ATP-SUV for alleviating the effects of cyanide poisoning. ATP-SUV can also be used to decrease the effects of carbon monoxide poisoning.

Biomolecule-SUV for Delivery of Proteins, Carbohydrates, Oligonucleotides, and Other Drugs The highly absorptive lipid vesicles disclosed herein can be made in the presence of water soluble and membrane bound proteins, carbohydrates, oligonucleotides, and other drugs, so that efficient delivery is obtained to the cytosol or to the cell membrane any of the aforementioned substances. This method of drug delivery can circumvent many traditional problems, and (1) allows for the introduction of pharmaceuticals that are membrane impermeable, thus greatly expanding the range of pharmaceuticals that can be used, as well as increasing the efficacy of those that have a low rate of membrane penetration; and (2) allows for the incorporation of polypeptides and carbohydrates directly into cell membranes. This last advantage allows, for example, replacement therapies that circumvent uncertain gene therapy approaches. For example, if a subject lacks a receptor on a cell, that receptor can be incorporated into a lipid vesicle disclosed herein and administered appropriately.

These methods mimic those methods that introduce ATP into cells, except that the SUVs contain either the substance within the vesicle, and/or membrane-incorporated molecules.

ATP-SUV for Other Low Oxygen Situations

Underwater diving, space travel, high altitudes, and other situations where oxygen is rare can lead to decreases in oxygen delivery to the body. To compensate for the oxygen deficit, ATP-SUV is administered intravenously, orally, or by inhalation.

ATP-SUV for Meat Preservation

In addition to its uses in tissue and organ preservation, and animals and patients, ATP-SUV can keep cells in meat alive in the absence of oxygen. After slaughter, the animal is bled and residual blood is flushed from the carcass. ATP-SUV is infused into the animal via the carotid or other large artery, filling the vasculature with ATP-SUV. The animal is then shipped with the ATP-SUV in place, keeping the cells of the animal alive and thus extending the shelf life of the meat, much as ATP-SUV extends the shelf life of blood. Since ATP-SUV makes use of endogenous components, the taste and texture of the meat is not affected.

ATP-SUV for Plants

Plants utilize photosynthesis in order to sustain life and growth. Photosynthesis can be divided into two reactions: the light reaction, which harvests energy from sunlight and converts it to chemical energy, ATP and the reduced form of nicotainamide adenine dinucleotide phosphate (NADPH); and the dark reaction, which uses ATP and NADPH to fix $CO_2$.

Plants are provided with ATP-SUV via either the root system or applied directly to the leaves, stems, flowers, meristems or other plant parts. ATP-SUV delivers the ATP necessary for the dark reactions to the plant cells. The delivery of ATP using ATP-SUV reduces or by-passes the need for sunlight, enabling them to grow in the dark or under less-bright conditions. In addition, the ATP-SUV increases plant growth and sustains plant life, important aspects to fresh vegetables at market, the cut-flower industry, and hydroponic gardening.

ATP-SUV for Bioreactors

The major limiting factor for bioreactor productivity is that bacteria and yeast, the primary producers of molecules from bioreaction, must have sufficient substrate to make ATP. Thus, the number of bacteria or yeast is limited in any one culture. ATP-SUV is infused into the bioreactor to increase the number of microorganisms, increasing output of the bioreactor. This application is not limited to bacteria and fungi, since cultured insect, animal, plant and other eukaryotic cells have the similar requirement for ATP production.

EXAMPLES

The following examples are provided to illustrate the presently disclosed subject matter. Those skilled in the art can readily make insignificant variations in the compositions and methods of the presently disclosed subject matter. The examples are not meant to limit the present subject matter in any way.

Example 1

Construction of Lipid Vesicles

Vesicles were constructed from 1,2-dioleoyl-sn-glycero-3-phosphocholine (DOPC); 1,2-dioleoly-sn-glycero-3-ethylphosphocholine (DOPC-e) and 1-palmitoyl-2-oleoyl-sn-glycero-3-phosphate (POPA) lipids. (all from Avanti Polar Lipids; Alabaster, Ala.). The lipids were used without further purification. After dissolving the lipids in chloroform and placed in a glass test tube, the chloroform was removed by evaporation under a steady stream of nitrogen gas, followed by overnight vacuum pumping. The dried lipid material was re-hydrated in HBSS experimental buffer (Sigma; St. Louis, Mo.) above its phase transition temperature (25° C.) for 30 minutes. Two glass beads were added to the buffer/lipid mixture, and the suspension vortexed for five minutes to create multilamellar vesicles. The milky solution was then sonicated using a microtip Branson Sonifier 450, with the microtip placed in the test tube. The vesicles were then sonicated for five minutes at level 5 with a 40% duty cycle to create small unilamellar vesicles (SUVs).

Example 2

Encapsulation of ATP

To demonstrate incorporation of ATP into the vesicles of Example 1, 30 µCi of $^3$H-ATP (Amersham; Arlington Heights, Ill.) was added to the experimental buffer prior to creating the multilamellar vesicles. The suspension was passed over a Sephadex G-25 (Sigma) column (1 cm×40 cm) to remove the non-encapsulated ATP. The vesicles were collected in the first 50 ml of the effluent. The percent encapsulation was determined by measuring the radioactivity contained within the vesicles and in the supernatant by liquid scintillation counting. Vesicles comprising DOPC, DOPC:DOPC-e (1:1), DOPC:POPA (50:1) and DOPC:POPA (1:1) all gave approximately the same percent encapsulation of ATP, varying between 1 to 2.5% of the original amount of ATP in solution.

Example 3

Rate of Absorption of Vesicles to HUVEC and Release of Encapsulated Contents into the Cytoplasm To determine the absorptive rate (e.g., fusion rate) of SUVs, SUVs were loaded with a fluorescent probe, presented to cells in vitro, washed, and then analyzed for cellular fluorescence.

Human umbilical vein endothelial cells (HUVEC) were purchased from BioWhitaker (Walkersville, Md.) at passage I and cultured until passage 8, after which they were no longer used. HUVEC were grown in endothelial cell growth medium (EGM; BioWhitaker) to confluence on 12-well culture dishes in EGM medium. The HUVEC were then washed 3 times with HBSS. Lipid vesicles were made as in Example 1, but 1 mM carboxyfluorescein was loaded into the vesicles. The vesicles were then incubated with the cells for either 5, 10, 30, 45, 60, 90, 120 or 240 minutes at 37° C. in a humidified $CO_2$ incubator, after which the vesicles were washed from the cells, and the cells removed from the dish by gentle treatment with trypsin. The fluorescence of carboxyfluorescein in the HUVEC was measured using a Perkin-Elmer LS50B Luminescence Spectrophotometer (Wellesly, Mass.), using an excitation of 495 nm and emission of 520 nm. In some experiments, cells were not trypsinized, and photomicrographs of the cells were taken in order to demonstrate the homogeneity of the absorption event. The range of fluorescent units (FUs) for this experiment was 0 to 450 units. The rate of absorption highly depended on the lipid composition of the SUVs. DOPC showed little or no absorption at all for the first 30 minutes, after which the absorption rate became logarithmic, reaching approximately 350 FUs. In contrast, DOPC:DOPC-e (1:1) gave a much faster initial rate of absorption and a slower final rate of absorption (approximately 35 FUs at 5 minutes; approximately 100 FUs at 120 minutes). The fastest rate of absorption was found using DOPC:POPA (1:1), which showed significant delivery of carboxyfluorescein within 5 minutes. As designed, the absorption rate of the three vesicles can be characterized as fast, medium and slow.

One issue which was resolved was whether the vesicles were actually fusing with the cells or simply aggregating on the cell surface. To examine this, HUVEC exposed to lipid vesicles and not removed from the culture wells were examined for the distribution of fluorescence by fluorescent microscopy. Cells exposed to all three compositions showed diffuse fluorescence throughout the cells after 5 minutes rather than punctate fluorescence, which would have suggested that lysosomes were sequestering the vesicles, thereby preventing cellular access to the carboxyfluorescein. Alternatively, the vesicles were aggregating on the cell surface. These results demonstrate that lipid vesicles fused to the cells and released the encapsulated contents within the cytoplasm rather than aggregating on the cell surface or being sequestered by lysosomes.

To determine if ATP is also introduced into cells like carboxyfluorescein, vesicle absorption and release of ATP into HUVEC was followed using the $^3$H-ATP-containing vesicles of Example 2. The vesicles were incubated with HUVEC for 5, 10, 15, 30, 45, 60, 90, 120, or 240 minutes. The result shown in FIG. 1 is the partition coefficient of ATP inside the cells after 1 hour. DOPC/POPA gave the largest percent incorporation at this distant time period, followed by DOPC/DOPC-e, then $^3$H-ATP only, without vesicles. When the cells were washed repeatedly there was a significant change in the radioactivity of the cells. DOPC showed a slight but significant decrease in radioactivity; DOPC/DOPC-e showed no decrease in radioactivity after repeated washes, while free $^3$H-ATP showed a complete loss of radioactivity, confirming the observation that free ATP is unable to penetrate the cell membrane. These data, taken together with the fusion data, indicate that DOPC vesicles are being endocytosed, DOPC:DOPC-e vesicles are fusing, and free ATP does not enter cells. DOPC:POPA vesicles also could not be washed away, indicating that they also were fusing with cells and delivering the encapsulated contents into the cytoplasm.

Example 4

Endothelial Macromolecular Permeability

Any use of the vesicles of the presently disclosed subject matter to deliver encapsulated molecules in vivo through the circulatory system in contrast to delivering molecules directly to cells requires that the vesicles and/or molecules must penetrate the vascular endothelium. The vascular endothelium constitutes a barrier, but the cell-to-cell barrier can be bridged, as for example, when leukocytes leave the circulation and enter the interstitial space. In order to address this issue, the effect of the lipid vesicles of the present subject matter on endothelial permeability was measured.

HUVEC were grown to confluence on microporous filters (0.8 μm) in EGM. The cells were placed in a special chamber which allowed for the measurement of protein flux across the endothelial monolayer. The tracer used to examine the effects of the lipid vesicles on endothelial permeability was FITC-albumin (1 mg/ml). The FITC-albumin and the lipid vesicles were added to the endothelial cells at time zero. Every 5 minutes, a 500 μl sample of the supernatant was collected and then analyzed for fluorescence using the Perkin-Elmer LS 5OB Luminescence Spectrophotometer. DOPC vesicles had no effect on permeability, while HUVEC permeability increased in the presence of DOPC/DOPC-e, indicating that these vesicles created small gaps between adjacent endothelial cells.

Example 5

Metabolic Demand for ATP

As an example of determining the required optimum rate, the metabolic demand for ATP of rat liver cells was determined. Whole rat liver was isolated and placed in an isolation buffer (0.25 M sucrose, 0.04 M Tris at pH 7.2), minced with sterile scissors, and pieces of connective tissue were carefully trimmed. The liver was then passed through a #60 stainless steel wire mesh sieve, and the cellular effluent was collected on ice. The suspension was centrifuged at 4° C. for five minutes to pellet the cells. The supernatant was discarded, and the cells were re-suspended in oxygenation buffer (200 mM sucrose, 70 mM KCL, 5 mM maleate and 40 mM Tris, pH 7.3). Five milliliters of oxygenation buffer was placed in a Yellow Springs Instruments Oxygen Meter (Yellow Springs, Ohio) and allowed to equilibrate to 37° C. Fifty μl of the cell extract was placed in the chamber, achieving a 2-3 mg/ml final protein concentration. Baseline oxygen consumption was then monitored for 1 minute, after which 100 mM ADP was added to the cells, and State 2 respiration was measured. Next, 5 mM glutamate was added, and State 3 respiration was measured. The ADP/$O_2$ ratio was determined by measuring the amount of ADP added to the amount of oxygen consumed. Thus the State 3 respiration is a measure of how much ATP is consumed by the cells/minute/mg of tissue.

Example 6

ATP-SUV Accelerates Wound Healing

Superficial wounds (approximately 80 mm² circles) were inflicted to the integument on nude mice at the upper cranial area. ATP-SUV was then applied to the wound twice daily to provide the border cells of the wound with ATP. The ATP-SUV was placed directly over the wound in a specially designed applicator which kept the water-based ATP-SUV in direct contact with the wound.

Figure 2:
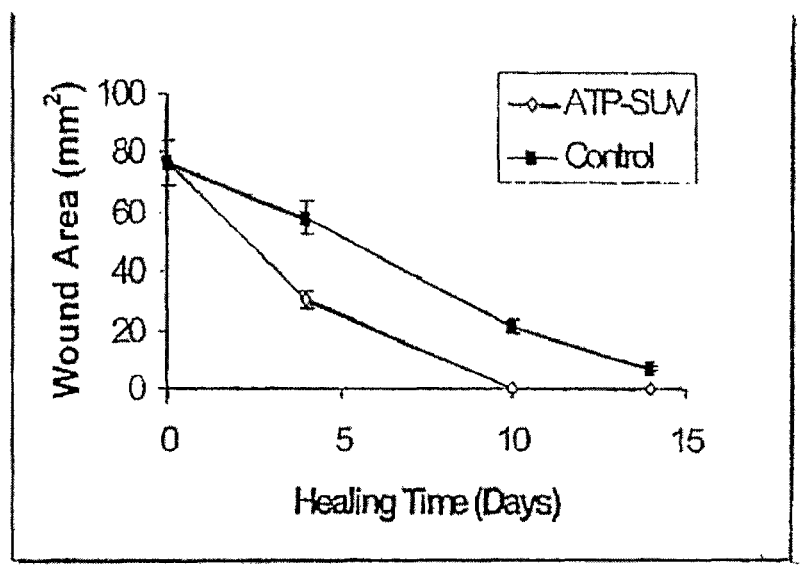
FIG. 2 is a line graph showing the effects of the compositions of the presently disclosed subject matter on wound healing, in a nude mouse.

As seen in FIG. 2, wounds treated with ATP-SUV compared to those treated with control substances healed more quickly. The curve for ATP-SUV-treated wounds, plotting wound area against healing time, demonstrates a logarithmic curve, while controls showed a more linear rate of healing. On Day 4, a difference of approximately 30 mm² is observed between the ATP-SUV treatment (≈30 mm²; less than half of the original wound area) and the control treatment (≈60 mm²); while at day 10, the wound area is virtual gone in ATP-SUV treated wounds, but not in control treated wounds (≈25 mm²). Qualitatively, Day 4 of ATP-SUV treated wounds resembled those of Day 10 in controls; while Day 10 mimicked the controls at Day 17. The wound was healed by Day 17 in wounds treated with ATP-SUV, while controls on this day were not yet completely healed.

Example 7

Limb Reattachment

Hind legs were amputated from rats, and the major feed arteries for the severed limbs were cannulated for infusion of ATP-SUV, (1 mM ATP) solution. The limbs were perfused with ATP-SUV or control solutions (see Table 1) every 3 hours, or as deemed necessary by the change in tissue ATP levels. The arterial pressure of the limbs was monitored during infusion to decrease the chance of flow-induced injury, and to monitor the overall preservation of the severed limbs (higher perfusion pressures may indicate limb morbidity). Following the preservation period, the limbs were flushed with Ringers to remove traces of ATP-SUV. The limbs were then surgically reattached, and external indices of limb function after anastomoses were evaluated (limb color, evidence of microthrombi, coagulation, limb temperature). The animals prior to and following replantation received heparin to prevent hemostasis. In addition, animals were placed on antibiotic therapy to reduce infection. Control limbs were perfused with vehicle only, vehicle and ATP only, or vehicle and SUVs only.

Figure 3:
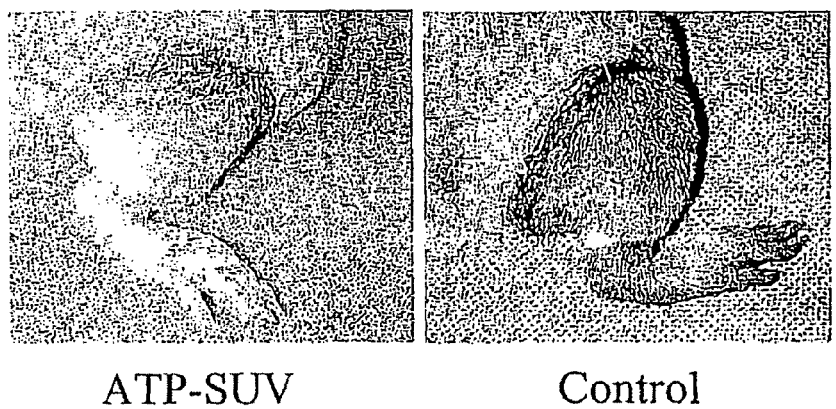
FIG. 3 is a pair of photographs showing the successful replantation of an amputated limb in a rat. The limb is fully functional after re-attachment.

After 21 hours post-replantation, the ATP-SUV-treated limb exhibited a healthy pink color and had re-attained physiological temperature. After more than 150 days, those animals that received ATP-SUV-treated limbs were using these limbs as if the limb had never been amputated. The only qualitative side effect was a curling of the toes, most likely due to the lack of physical therapy, which most likely would have corrected this minor defect. In the controls, however, the limbs were darkly-colored and cold to the touch, exhibiting signs of necrosis. Histological examination of the hind limbs after preservation indicated that the ATP-SUV group had maintained endothelial cell and muscle cell viability. All controls had non-viable endothelium and muscle. The summary of these results is shown in Table 1. Qualitative results are shown in FIG. 3.

TABLE 1

Summary of results from limb replantation studies

| Group | Limb outcome | n |
|---|---|---|
| Vehicle only | necrosis | 2 |
| Vehicle and 1 mM ATP only | necrosis | 2 |
| Vehicle and SUVs only | necrosis | 2 |
| Vehicle and ATP-SUV | survival | 5 |

Example 8

ATP-SUV Protects Isolated Hearts from Hypoxia

Hearts removed from rats were monitored using a Lagendorff heart perfusion apparatus. The hearts were cannulated and placed in a specially designed chamber, which perfused the heart, and allowed for the injection of ATP-SUV. The oxygenated perfusate, which was circulating to the heart was stopped, and ATP-SUV was injected into the heart. The heart was then placed in arrest by injecting a high potassium solution. The ATP-SUV was kept in the heart for 120 minutes at 37° C. under no-flow conditions. The heart was then flushed with oxygenated perfusate solution, and the performance of the heart was monitored. ATP-SUV treated hearts regained heart function compared to controls.

Example 9

ATP-SUV Increases Survival Rates after Hemorrhagic Shock

Figure 7:
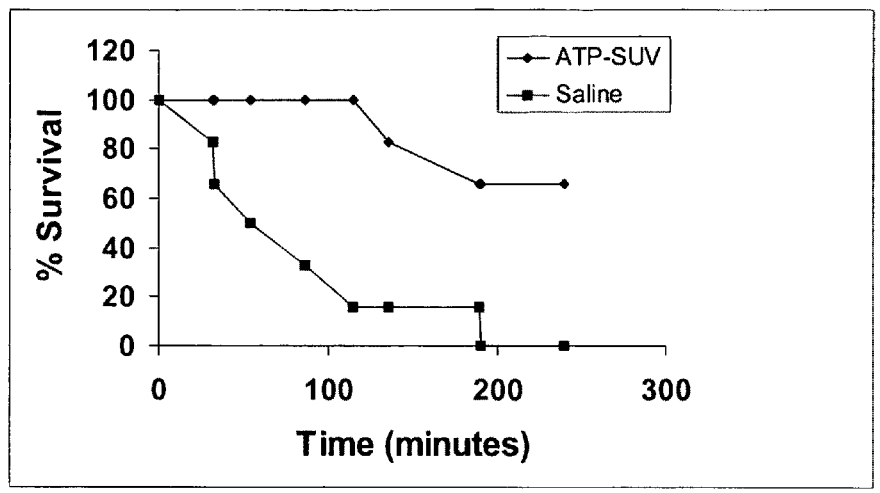
FIG. 7 is a line graph showing increased survival rates in a hemorrhagic shock model for animals administered ATP-SUV as compared to control animals.

Sprague-Dawley Rats (200-250 g) were anesthetized using pentobarbital. The carotid artery was cannulated and a pressure transducer was inserted for measurement of blood pressure and heart rate. The femoral artery was cannulated for blood letting. After a 30 min stabilization period, blood was withdrawn from the animal at a rate of 1 cc/min until 33% of the animals total blood supply was removed. The animals were kept at this reduced blood volume for a period of 60 minutes. At the end of the 60 minute period, lactated ringers saline (traditional crystalloid resuscitation) or ATP-SUV was given to the animals IP. The survival time, blood pressure and heart rate were monitored for an additional 120 minutes. At the end of the experiment the animal was euthanized and a sample of blood was removed for analysis of $pCO_2$, lactic acid, and measurements of high energy phosphates. ATP-SUV treated animals showed an increased survival rate across all time points when compared to saline treated control animals, as indicated by the data shown in FIG. 7. In addition, the ATP-SUV group had significantly lower pCO2, lactic acid, and had significant increases in blood and tissue high energy phosphate levels.

Example 10

ATP-SUV Increases Survival Rates after Chemically-Induced Hypoxia

Figure 8:
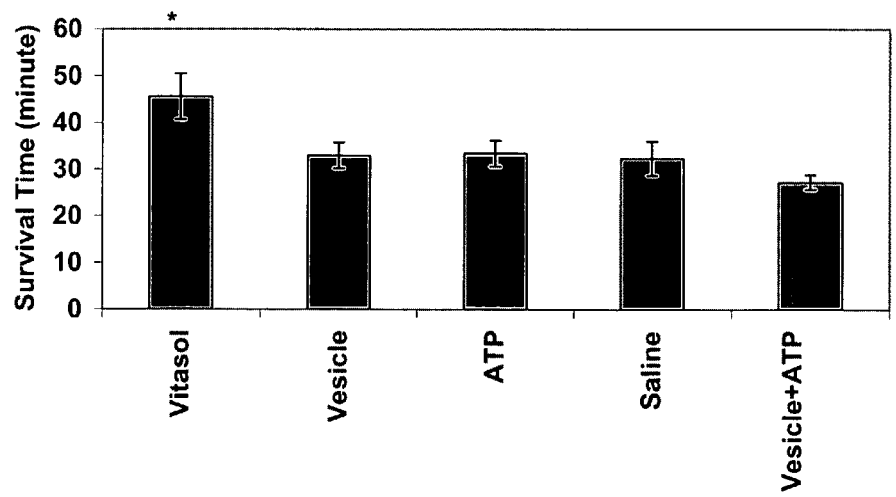
FIG. 8 is a bar graph showing increased survival rates in a chemically-induced hypoxia model for animals administered ATP-SUV as compared to control animals.

Sprague-Dawley rats (200-250 g) were anesthetized using pentobarbital. The carotid artery was cannulated and a pressure transducer was inserted for measurement of blood pressure and heart rate. The femoral artery was cannulated for administration of potassium cyanide (KCN) (2.5 mM). After a 30 minute stabilization period, the animal was given either ATP-SUV (labeled as "Vitasol" in FIG. 8) or lactated ringer's saline IP. Five minutes later a bolus of KCN was injected via the femoral artery. Survival time, blood pressure, and heart rate were measured over a 4 hr period. Results shown in FIG. 8 show increased survival rates for animals administered ATP-SUV compared to control animals.

Example 11

Improvement in Blood Storage

Prophetic Example

To ascertain whether ATP-containing vesicles preserve blood and whether the addition of the glycolytic intermediates phosphoenolpyruvate (PEP) and fructose-1,6-diphosphate (FDP) further improve viability, the following experiment is performed. Vesicles are constructed using DOPC only, following the methods of Example 2. Blood will be collected according to standard procedures into a bag containing a standard Dextrose-citrate-adenine-phosphate mixture (Baxter; Deerfield, Ill.). For each set of experiments, one unit of blood is divided into equal aliquots and is aseptically transferred to polyethylene bags containing no additional additives (control). Test substances will be added to the other aliquots as follows:

Control, no additives
Control, vesicles containing PEP, FDP and ribose
ATP-SUVs.

At 30, 45, 60 and 90 days, aliquots are withdrawn, and the condition of the red blood cells is evaluated according to the following parameters: ATP content, hematocrit, hemoglobin, and cell viability (using Trypan blue (Sigma) exclusion or LIVE/DEAD kit (Molecular Products; Eugene, Oreg.). Anticipated results: cells stored in the presence of ATP containing vesicles will be in better condition than the controls; that is, ATP content will be higher, pH will have decreased less (indicating less glycolysis), and the red blood cells will have retained the biconcave shape typical of a functional red blood cell.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

Alberts B, Johnson M A, Lewis J, Raff M, Roberts K, Walter P, (2002) Molecular Biology of the Cell. Garland Science, New York.

Ainscow, E. K., and Brand, M. D. (1999) Top-down control analysis of ATP turnover, glycolysis and oxidative phosphorylation in rat hepatocytes. Eur. J. Biochem. 263: 671-685.

Albrecht E W. Stegeman C A. Heeringa P. Henning R H. van Goor H. (2003) Protective role of endothelial nitric oxide synthase. Journal of Pathology. 199(1):8-17.

Arakawa A, Ishiguro S, Ohki K, Tamai M. (1998) Preparation of liposome-encapsulating adenosine triphosphate. Tohoku J Exp Med 184: 39-47.

Arii S. Imamura M. (2000) Physiological role of sinusoidal endothelial cells and Kupffer cells and their implication in the pathogenesis of liver injury. Journal of Hepato-Biliary-Pancreatic Surgery. 7(1):40-8.

Brand, M. D. (1995). Measurement of mitochondrial proton motive force. In Bioenergetics, a Practical Approach/ Brown, G. C., and Cooper, C. E., eds. Oxford University Press, Oxford. 39-62.

Childs J W, Lower R R. (1969) Preservation of the heart. Prog Cardiovasc Dis. 12:149-163.

Ehringer W, Niu W, Chiang B et al. (2000) Membrane permeability of fructose-1,6-diphosphate in lipid vesicles and endothelial cells. Mol Cell Biochem 210:35-45.

Ehringer W D, Chiang B, Chien S. (2001) The uptake and metabolism of fructose-1,6-diphosphate in rat cardiomyocytes. Mol Cell Biochem.; 221:33-40.

Ehringer W D, Su S, Chiang B et al. (2002) Destabilizing effects of fructose-1,6-bisphosphate on membrane bilayers. Lipids; 37:885-892.

Eltzschig H K. Collard C D. (2004) Vascular ischaemia and reperfusion injury. British Medical Bulletin. 70:71-86.

Jahn R, Sudhof T C. (1999) Membrane fusion and exocytosis. Annu Rev Biochem 68: 863-911.

Oku N. Namba Y. (1994) Long-circulating liposomes. *Critical Reviews in Therapeutic Drug Carrier Systems* 11(4): 231-70.

Puisieux F, Fattal E, Lahiani M, Auger J, Jouannet P, Couvreur P, Delattre J. (1994) Liposomes, an interesting tool to deliver a bioenergetic substrate (ATP). in vitro and in vivo studies. *J Drug Target* 2: 443-448.

Remington: the science and practice of pharmacy (2000) Alfonso R. Gennaro, chairman of the editorial board and editor. Edition: 20th ed. Lippincott Williams & Wilkins, Baltimore, Md.

It will be understood that various details of the presently disclosed subject matter may be changed without departing from the scope of the present subject matter. Furthermore, the foregoing description is for the purpose of illustration only, and not for the purpose of limitation.

What is claimed is:

1. Vesicles, comprising:
   (a) a first lipid that is a phosphatidylcholine; and
   (b) a second lipid having a structure selected from the group consisting of formulas (XXIV), (XXV), (XXVI), (XXVII), (XXIX), (XXXI), (XXXII), (XXXIII), and (XXXIV):

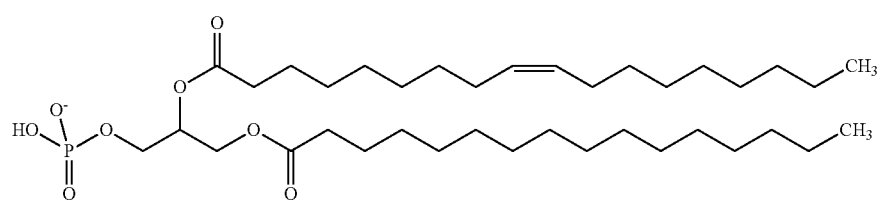

(XXIV)

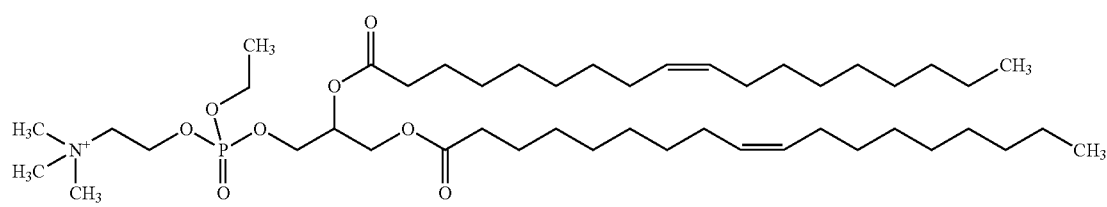

(XXV)

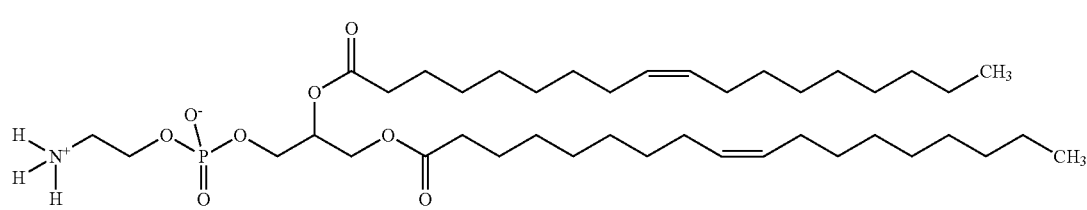

(XXVI)

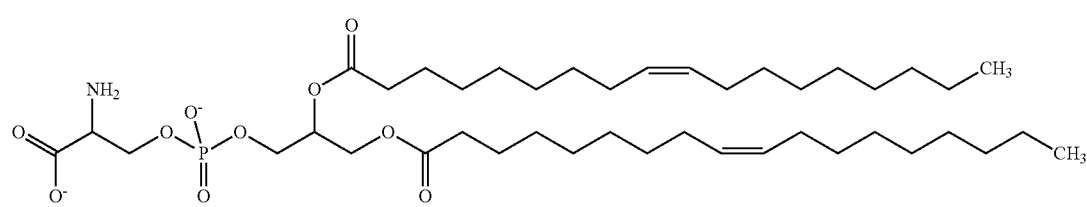

(XXVII)

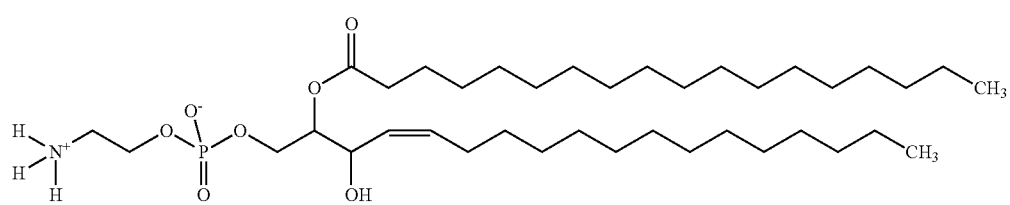

(XXIX)

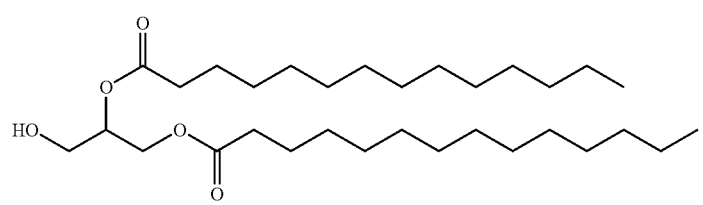

(XXXI)

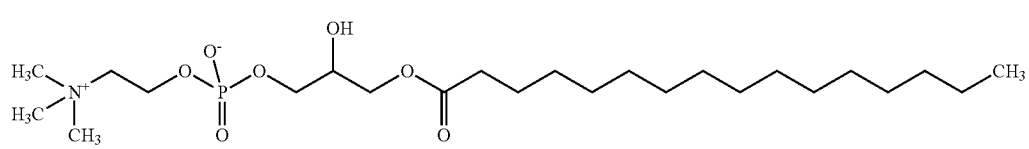
(XXXII)

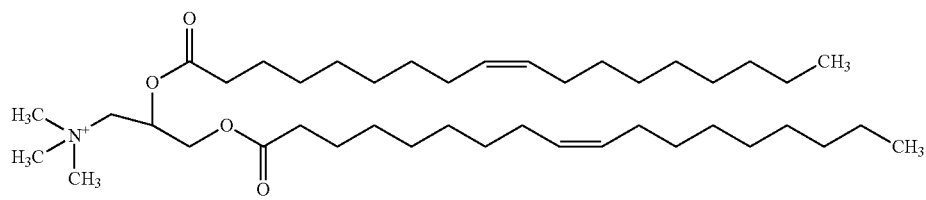
(XXXIII)

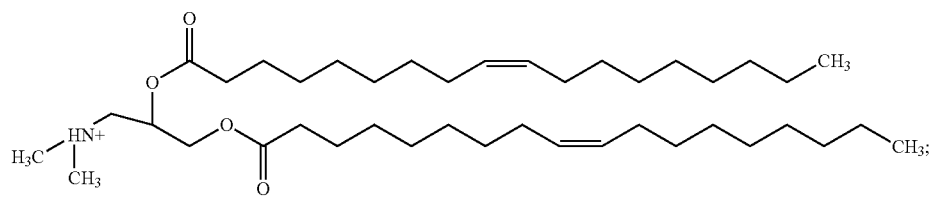
(XXXIV)

and
a high energy phosphate selected from the group consisting of adenosine triphosphate (ATP), adenosine diphosphate (ADP), adenosine monophosphate (AMP), cytosine triphosphate (CTP), cytosine diphosphate (CDP), cytosine monophosphate (CMP), uracil triphosphate (UTP), uracil diphosphate (UDP), uracil monophosphate (UMP), guanosine triphosphate (GTP), guanosine diphosphate (GDP), guanosine monophosphate (GMP), thymine triphosphate (TTP), thymine diphosphate (TDP), thymine monophosphate (TMP), inosine triphosphate (ITP), inosine diphosphate (IDP), inosine monophosphate (IMP), and phosphocreatine; and
wherein the vesicles are unilamellar, and wherein the vesicles an absorption rate of at least 1 vesicle absorption per second per cell when the vesicles are contacted with target cells.

2. The vesicles of claim 1, wherein the high-energy phosphate is ATP.

3. The vesicles of claim 2, wherein the ATP is Mg-ATP.

4. The vesicles of claim 2, wherein the ATP is present at a concentration of about 50 mM or less when the vesicle is in solution.

5. The vesicles of claim 4, wherein the ATP is present at a concentration of from about 0.001 mM to about 50 mM when the vesicles are in solution.

6. The vesicles of claim 5, wherein the ATP is present at a concentration of from about 1 mM to about 50 mM when the vesicles are in solution.

7. The vesicles of claim 1, wherein the vesicles an absorption rate of at least $10^3$ vesicle absorptions per second per cell when the vesicles are contacted with target cells.

8. The vesicles of claim 7, wherein the vesicle has an absorption rate of at least $10^6$ vesicle absorptions per second per cell when the vesicles are contacted with target cells.

9. The vesicles of claim 1, wherein the vesicles have a mole:mole ratio of the first lipid to the second lipid of 1:9 to 100,000:1.

10. The vesicles of claim 9, wherein the vesicles have a mole:mole ratio of the first lipid to the second lipid of 1:1 to 1,000:1.

11. The vesicles of claim 1, wherein the vesicles have hydrodynamic radii of from about 20 nm to about 600 nm.

12. The vesicles of claim 11, wherein the vesicles have hydrodynamic radii of from about 100 nm to about 300 nm.

13. The vesicles of claim 1, wherein the ATP is selected from the group consisting of Mg-ATP or Na-ATP.

14. The vesicles of claim 1, wherein the first lipid is selected from the group consisting of soy phosphatidylcholine and DOPC; and wherein the second lipid has the structure of formula (XXXIII).

15. The vesicles of claim 1, wherein the vesicles are freeze-dried.

16. The vesicles of claim 1, wherein the vesicles are formulated in a solution.

17. The vesicles of claim 16, wherein the vesicles are provided in the solution at a concentration of about 5 mg/ml.

18. The vesicles of claim 1, wherein the vesicles are formulated for topical delivery.

19. The vesicles of claim 1, wherein the vesicles are formulated for transdermal delivery.

20. The vesicles of claim 1, wherein the vesicles are provided in an ointment, salve, gel, or cream.

21. The vesicles of claim 16, wherein the vesicles are provided in the solution at a concentration of about 0.5 mg/ml-20 mg/ml.

22. The vesicles of claim 1, wherein the phosphatidylcholine is selected from the group consisting of soy phosphatidylcholine, egg phosphatidylcholine, E. coli extract 5 phosphatidylcholine, 1,2-dioleoyl-sn-glycero-3-phosphocholine (DOPC), 1-palmitoyl-2-docosahexaenoyl-sn-glycero-3-phosphocholine (PDPC), dimyristoyl phosphatidylcholine (DMPC), dipalmitoyl phosphatidylcholine (DPPC), distearoyl phosphatidylcholine (DSPC) and mixtures thereof.

23. The vesicles of claim 1, wherein the second lipid has the structure of formula XXXII.

24. A vesicle, comprising:
adenosine triphosphate (ATP);
soy phosphatidylcholine; and
1,2-dioleoyl-3-trimethylammonium-propane (DOTAP), wherein the vesicle is unilamellar.

25. The vesicle of claim 24, wherein the ATP is present at a concentration of from about 0.01 mM to about 50 mM when the vesicle is in solution.

26. The vesicle of claim 24, wherein the vesicle has a mole:mole ratio of soy phosphatidylcholine to DOTAP of 50:1.

27. The vesicle of claim 24, wherein the vesicle has a hydrodynamic radius of from about 100 nm to about 300 nm.

28. The vesicle of claim 24, wherein the vesicle has a hydrodynamic radius of from about 10 nm to about 600 nm.

29. The vesicle of claim 24, wherein the ATP is selected from Mg-ATP or Na-ATP.

30. The vesicle of claim 24, further comprising a lipid having the structure of formula XXXII.

31. A vesicle, comprising:
adenosine triphosphate (ATP);
1,2-dioleoyl-sn-glycero-3-phosphatidylcholine (DOPC) and
1,2-dioleoyl-3-trimethylammonium-propane (DOTAP), wherein the vesicle is unilamellar.

32. The vesicle of claim 31, wherein the ATP is present at a concentration of from about 0.01 mM to about 50 mM when the vesicle is in solution.

33. The vesicle of claim 31, wherein the vesicle has a mole:mole ratio of DOPC to DOTAP of 50:1.

34. The vesicle of claim 31, wherein the vesicle has a hydrodynamic radius of from about 100 nm to about 300 nm.

35. The vesicle of claim 31, wherein the vesicle has a hydrodynamic radius of from about 10 nm to about 600 nm.

36. The vesicle of claim 31, further comprising a lipid having the structure of formula XXXII.

37. A vesicle, comprising:
A first lipid that is a phosphatidylcholine;
A second lipid having the structure of formula XXXII

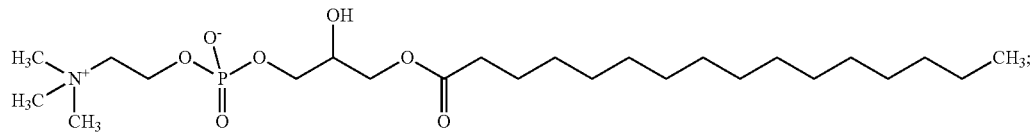

(XXXIII)

and
a high energy phosphate selected from the group consisting of adenosine triphosphate (ATP), adenosine diphosphate (ADP), adenosine monophosphate (AMP), cytosine triphosphate (CTP), cytosine diphosphate (CDP), cytosine monophosphate (CMP), uracil triphosphate (UTP), uracil diphosphate (UDO), uracil monophosphate (UMP), guanosine triphosphate (GTP), guanosine diphosphate (GDP), guanosine monophosphate (GMP), thymine triphosphate (TTP), thymine diphosphate (TDP), thymine monophosphate (TMP), inosine triphosphate (ITP), inosine diphosphate (IDP), inosine monophosphate (IMP), and phosphocreatine; and
wherein the vesicle is unilamellar.

38. A vesicle, comprising:
a high energy phosphate selected from the group consisting of adenosine triphosphate (ATP), adenosine diphosphate (ADP), adenosine monophosphate (AMP), cytosine triphosphate (CTP), cytosine diphosphate (CDP), cytosine monophosphate (CMP), uracil triphosphate (UTP), uracil diphosphate (UDP), uracil monophosphate (UMP), guanosine triphosphate (GTP), guanosine diphosphate (GDP), guanosine monophosphate (GMP), thymine triphosphate (TTP), thymine diphosphate (TDP), thymine monophosphate (TMP), inosine triphosphate (ITP), inosine diphosphate (IDP), inosine monophosphate (IMP), and phosphocreatinea phosphatidylcholine; and
1,2-dioleoyl-3-trimethylammonium-propane (DOTAP), wherein the vesicle is unilamellar.

39. The vesicle of claim 38, wherein the high energy phosphate is ATP.

40. The vesicle of claim 38, wherein the phosphatidylcholine is soy phosphatidylcholine, egg phosphatidylcholine, E. coli extract 5 phosphatidylcholine, 1,2-dioleoyl-sn-glycero-3-phosphocholine (DOPC), 1-palmitoyl-2-docosahexaenoyl-sn-glycero-3-phosphocholine (PDPC), dimyristoyl phosphatidylcholine (DMPC), dipalmitoyl phosphatidylcholine (DPPC), distearoyl phosphatidylcholine (DSPC) or a mixture thereof.

41. The vesicle of claim 38, wherein the vesicle is freeze-dried.

42. The vesicle of claim 38, wherein the vesicle is formulated in a solution.

43. The vesicle of claim 42, wherein the vesicle is provided in the solution at a concentration of about 0.5 mg/ml-20 mg/ml.

44. The vesicle of claim 38, wherein the vesicle is provided in an ointment, salve, gel, or cream.

45. A method of delivering a high energy phosphate to a cell, comprising contacting the cell with the vesicles of claim 1,
wherein the high energy phosphate is selected from the group consisting of adenosine triphosphate (ATP), adenosine diphosphate (ADP), adenosine monophosphate (AMP), cytosine triphosphate (CTP), cytosine diphosphate (CDP), cytosine monophosphate (CMP), uracil triphosphate (UTP), uracil diphosphate (UDP), uracil monophosphate (UMP), guanosine triphosphate (GTP), guanosine diphosphate (GDP), guanosine monophosphate (GMP), thymine triphosphate (TTP), thymine diphosphate (TDP), thymine monophosphate (TMP), inosine triphosphate (ITP), inosine diphosphate (IDP), inosine monophosphate (IMP), and phosphocreatine.

46. The method of claim 45, wherein the biomolecule is ATP.

47. The method of claim 46, wherein an amount of ATP delivered to the cell is sufficient to meet metabolic demand of the cell.

48. A method for treating a wound, the method comprising contacting the wound with a composition comprising the vesicles of claim 1.

49. The method of claim 48, wherein the composition further comprises becaplermin, fibroblast growth factor, vascular endothelial growth factor, an antibiotic, silver containing compositions, a skin graft composition or combinations thereof.

50. The method of claim 48, the method further comprising contacting the wound with a skin graft composition.

51. A method of preserving tissue, comprising contacting tissue with the vesicles of claim 1.

\* \* \* \* \*